US010450462B2

(12) United States Patent
Shida et al.

(10) Patent No.: US 10,450,462 B2
(45) Date of Patent: Oct. 22, 2019

(54) COLORED COMPOSITION

(71) Applicant: WAKO PURE CHEMICAL INDUSTRIES, LTD., Osaka-shi, Osaka (JP)

(72) Inventors: Yukihiko Shida, Kawagoe (JP); Taeyeon Kim, Kawagoe (JP); Tomotaka Totsuka, Kawagoe (JP); Masahiro Takano, Kawagoe (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 392 days.

(21) Appl. No.: 14/767,819

(22) PCT Filed: Feb. 13, 2014

(86) PCT No.: PCT/JP2014/053367
§ 371 (c)(1),
(2) Date: Aug. 31, 2015

(87) PCT Pub. No.: WO2014/126167
PCT Pub. Date: Aug. 21, 2014

(65) Prior Publication Data
US 2016/0040013 A1 Feb. 11, 2016

(30) Foreign Application Priority Data

Feb. 15, 2013 (JP) ................. 2013-027927

(51) Int. Cl.
| | |
|---|---|
| *C09B 62/465* | (2006.01) |
| *C07D 311/82* | (2006.01) |
| *C07F 5/02* | (2006.01) |
| *C08F 220/36* | (2006.01) |
| *G02B 5/22* | (2006.01) |
| *C07C 309/30* | (2006.01) |
| *C07C 309/31* | (2006.01) |
| *C07C 309/39* | (2006.01) |
| *C07C 309/40* | (2006.01) |
| *C09B 11/24* | (2006.01) |
| *C09B 69/06* | (2006.01) |
| *C09B 69/10* | (2006.01) |
| *C08F 220/18* | (2006.01) |
| *C07D 311/84* | (2006.01) |
| *C07C 309/29* | (2006.01) |
| *C08F 20/18* | (2006.01) |
| *C08F 120/18* | (2006.01) |
| *C08F 20/36* | (2006.01) |
| *C07D 311/88* | (2006.01) |
| *C09B 62/36* | (2006.01) |
| *C09B 62/44* | (2006.01) |
| *C07D 311/90* | (2006.01) |
| *C07D 311/86* | (2006.01) |

(52) U.S. Cl.
CPC .......... *C09B 62/465* (2013.01); *C07C 309/30* (2013.01); *C07C 309/31* (2013.01); *C07C 309/39* (2013.01); *C07C 309/40* (2013.01); *C07D 311/82* (2013.01); *C07F 5/02* (2013.01); *C08F 220/18* (2013.01); *C08F 220/36* (2013.01); *C09B 11/24* (2013.01); *C09B 69/06* (2013.01); *C09B 69/103* (2013.01); *G02B 5/223* (2013.01); *C07C 309/29* (2013.01); *C07D 311/84* (2013.01); *C07D 311/86* (2013.01); *C07D 311/88* (2013.01); *C07D 311/90* (2013.01); *C08F 20/18* (2013.01); *C08F 20/36* (2013.01); *C08F 120/18* (2013.01); *C09B 62/36* (2013.01); *C09B 62/365* (2013.01); *C09B 62/44* (2013.01)

(58) Field of Classification Search
CPC ....... C09B 62/36; C09B 62/365; C09B 62/44; C09B 62/465; C09B 11/24; C09B 69/06; C09B 69/103; C08F 220/18; C08F 20/18; C08F 120/18; C08F 220/36; C08F 12/036; C08F 20/36; C07C 309/31; C07C 309/29; C07C 309/39; C07D 311/82; C07D 311/84; C07D 311/86; C07D 311/88; C07D 311/90
See application file for complete search history.

(56) References Cited

U.S. PATENT DOCUMENTS

| 5,380,924 A | 1/1995 | Heiliger et al. |
| 5,587,443 A | 12/1996 | Heiliger et al. |

(Continued)

FOREIGN PATENT DOCUMENTS

| JP | 5-306266 A | 11/1993 |
| JP | 10-60298 A | 3/1998 |

(Continued)

OTHER PUBLICATIONS

International Search Report dated Apr. 15, 2014, issued in counterpart Application No. PCT/JP2014/053367 (2 pages).

*Primary Examiner* — Ling Siu Choi
*Assistant Examiner* — David L Miller
(74) *Attorney, Agent, or Firm* — Westerman, Hattori, Daniels & Adrian, LLP

(57) ABSTRACT

The present invention is to provide a colored composition having higher heat resistance compared with conventional colored compositions. The present invention further relates to: "a polymer having a monomer unit derived from a monomer which has (i) a cationic rhodamine derivative having, as an counter anion, an anion including an aryl group having an electron-withdrawing substituent and an anion group and (ii) an ethylenically unsaturated bond", "a monomer which has (i) a cationic rhodamine derivative having, as an counter anion, an anion including an aryl group having an electron-withdrawing substituent and an anion group and (ii) an ethylenically unsaturated bond", "a colored composition comprising the above-described polymer or the monomer", and "a colored composition for a color filter comprising the above-described polymer or the monomer".

17 Claims, No Drawings

(56) References Cited

U.S. PATENT DOCUMENTS

| | | | | |
|---|---|---|---|---|
| 6,080,516 A | * | 6/2000 | Devlin | C07D 487/04 106/494 |
| 7,498,123 B2 | * | 3/2009 | Cahill | B41M 5/465 430/108.2 |
| 2006/0021546 A1 | * | 2/2006 | Wu | C09D 11/34 106/31.29 |
| 2006/0089422 A1 | | 4/2006 | Vasudevan | |
| 2008/0275224 A1 | * | 11/2008 | Ignatyev | C07D 241/46 534/611 |

FOREIGN PATENT DOCUMENTS

| | | | |
|---|---|---|---|
| JP | 2000-103975 A | | 4/2000 |
| JP | 2000103975 A | * | 4/2000 |
| JP | 2006-176756 A | | 7/2006 |
| JP | 2012-83651 A | | 4/2012 |
| WO | 2008/087915 A1 | | 7/2008 |

\* cited by examiner

COLORED COMPOSITION

TECHNICAL FIELD

The present invention relates to a polymer which is used in the application forming a colored pixel of a color filter etc., the application of printing ink, ink-jet ink, and paint etc. and a colored composition comprising said polymer.

BACKGROUND ART

As the method forming the colored pixel in manufacturing a color filter of liquid crystal display device and solid-state image sensing device etc., a dyeing method or a dye-dispersion method employing a dye for the colorant, a pigment-dispersion method using a pigment, an electrode-position method, a printing method etc. are known. In recent years, as a characteristic of the color filter, improvement of brightness and contrast is particularly required. According to the pigment-dispersion method using a pigment, because of high heat resistance and light resistance as compared to a dye, deterioration is less in heating process in manufacturing a panel, and also a color pixel high having the long-term reliability can be obtained. Therefore, recently, pigment-dispersion method has become the mainstream. However, when pigment is used, because pigment itself has particle size there was a problem that contrast may be decreased by scattering of light. Although an attempt has also been made to micronize the pigments, there is a limit in micronization, and it has also been a problem to secure the dispersion stability of the micronized pigment.

On the other hand, as a method that can resolve these problems, the method forming the color pixel using a dye is now being studied. When the dye is used, the contrast is improved because light scattering is suppressed. However, because the dye has low heat resistance, and sublimation depending on the type, as compared to pigment, there were problems, such as reduction in brightness, fading, hue change. Therefore, in the method using the dye, it has been required to resolve this problem. Regarding the color filter using dye, various reports have been reported, for example, in JP-A-2012-83651, the colored resin composition using a rhodamine derivative as the dye has been reported.

CITATION LIST

Patent Literature

PATENT LITERATURE 1: JP-A-2012-83651

SUMMARY OF INVENTION

Technical Problem

Although we studied the colored resin composition using the rhodamine derivative reported by JP-A-2012-83651, heat resistance in the practical range was not obtained. Therefore, the present invention is to provide the colored composition having higher heat resistance than that of the conventional colored composition.

Solution to Problem

In view of the above-situation, the present inventors, as a result of intensive study, found that the colored composition having the excellent heat resistance and the less dye elution is obtained by using the compound which has the cationic rhodamine derivative having specific anion, as a counter anion, and ethylenically unsaturated bond, or the polymer having a monomer unit derived from the compound, as the dye, and have completed the present invention.

That is, the present invention relates to: "a polymer having a monomer unit derived from a compound which has (i) a cationic rhodamine derivative having, as an counter anion, an anion including an aryl group having an electron-withdrawing substituent and an anion group and (ii) an ethylenically unsaturated bond", "a compound which has (i) a cationic rhodamine derivative having, as an counter anion, an anion including an aryl group having an electron-withdrawing substituent and an anion group and (ii) an ethylenically unsaturated bond", "a colored composition comprising the above-described polymer or the compound", and "a colored composition for a color filter comprising the above-described polymer or the compound".

Advantageous Effects of Invention

When the polymer or the compound of the present invention is used as a colorant, even if heating is carried out at 230° C. for 30 minutes, the fading by heating is less, and excellent heat resistance effect is accomplished. That is, the colored composition containing the polymer or the compound of the present invention has superior heat resistance effect than the conventional colored composition.

In addition, when these were used by mixing into a resist material as colorant, the polymer or the compound of the present invention accomplishes the effect that dye (colorant) elution is less. Therefore, comparing with the conventional colored composition, it enables to provide the excellent colored composition not having problem, such as reduction of color concentration or color mixture.

DESCRIPTION OF EMBODIMENTS

[Anion Including an Aryl Group Having Electron-withdrawing Substituent and an Anion Group]

Anion group in anion which the cationic rhodamine derivative has (hereinafter, it may be abbreviated as anion pertaining to the present invention), includes, for example, a sulfonate anion group, a quaternary boron anion group, a nitrate ion, a phosphate ion etc., and a sulfonate anion group, a quaternary boron anion group are preferable, and a quaternary boron anion group is more preferable.

The electron-withdrawing substituent in anion pertaining to the present invention includes, for example, a halogenated alkyl group of 1 to 3 carbon atoms, a halogeno group, a nitro group, etc., among them, a halogeno group, a nitro group are preferable, and a halogeno group is particularly preferable.

Said halogenated alkyl group of 1 to 3 carbon atoms includes, for example, a chloroalkyl group, such as a chloromethyl group, a trichloromethyl group, a 2-chloroethyl group, a 2,2,2-trichloroethyl group, a 2-chloropropyl group, a 3-chloropropyl group, a 2-chloro-2-propyl group; a bromoalkyl group, such as a bromomethyl group, a tribromomethyl group, a 2-bromoethyl group, a 2,2,2-tribromoethyl group, a 2-bromopropyl group, a 3-bromopropyl group, 2-bromo-2-propyl group; a iodoalkyl group, such as a iodomethyl group, a triiodomethyl group, a 2-iodoethyl group, a 2,2,2-triiodoethyl group, a 2-iodopropyl group, a 3-iodopropyl group, a 2-iodo-2-propyl group; a fluoroalkyl group, such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3, 3-tetrafluoropropyl group, a heptafluoropropyl group. Among them, a fluoroalkyl group is preferable, and a trifluoromethyl group is particularly preferable.

The above-described halogeno group includes a fluoro group, a chloro group, a bromo group, a iodo group, and a fluoro group is preferable.

As the electron-withdrawing substituent in anion pertaining to the present invention, among the above-described specific examples, the one having strong electron-withdrawing force is preferable, a trifluoromethyl group, a fluoro group, and a nitro group are preferable, and a fluoro group and a nitro group are more preferable.

An aryl group in anion pertaining to the present invention includes, for example, a phenyl group, a naphthyl group, etc., and a phenyl group is preferable.

An aryl group having electron-withdrawing substituent in anion pertaining to the present invention includes, for example, the following general formula (XI) and (XII).

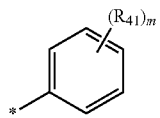
(XI)

(wherein, m represents an integer of 1 to 5, m pieces of $R_{41}$ each independently represent a halogenated alkyl group of 1 to 3 carbon atoms, a halogen atom or a nitro group, and * represents binding arm.)

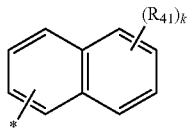
(XII)

(wherein, k represents an integer of 1 to 7. $R_{41}$ and * are the same as the above-described one. k pieces of $R_{41}$ may be the same or different ones.)

m is usually an integer of 1 to 5. When $R_{41}$ is a halogen atom, 2 to 5 is preferable, 3 to 5 is more preferable, 5 is further preferable. When $R_{41}$ is a nitro group, 1 to 3 is preferable, 1 is more preferable. When $R_{41}$ is a halogenated alkyl group, 1 to 5 is preferable.

k is usually an integer of 1 to 7, when $R_{41}$ is a halogen atom, 2 to 7 is preferable. When $R_{41}$ is nitro group, 1 to 3 is preferable, 1 is more preferable. When $R_{41}$ is a halogenated alkyl group, 1 to 7 is preferable.

A halogenated alkyl group of 1 to 3 carbon atoms of $R_{41}$ in the general formula (XI) and the general formula (XII) includes the same one as a halogenated alkyl group of 1 to 3 carbon atoms in the electron-withdrawing substituent in anion pertaining to the above-described present invention, also, the preferable one is same.

A halogen atom in the general formula (XI) and the general formula (XII) includes a fluorine atom, a chlorine atom, a bromine atom, a iodine atom, etc., among them, a fluorine atom is preferable.

The preferable specific example of $R_{41}$ in the general formula (XI) and the general formula (XII) is the same as the preferable one of the electron-withdrawing substituent anion pertaining to the above-described present invention.

The group represented by the general formula (XI) specifically includes, for example, a trifluoromethylphenyl group, a di(trifluoromethyl)phenyl group, a tri(trifluoromethyl)phenyl group, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a periodophenyl group, a nitrophenyl group, a dinitrophenyl group, a trinitrophenyl group, etc., and a difluorophenyl group, a trifluorophenyl group, perfluorophenyl group, etc., are preferable, a perfluorophenyl group is more preferable.

The group represented by the general formula (XII) specifically includes, for example, a trifluoromethylnaphthyl group, a di(trifluoromethyl)naphthyl group, a tri(trifluoromethyl)naphthyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthylgroup, a perbromonaphthyl group, a monoiodonaphthyl group, a diiodonaphthyl group, a triiodonaphthyl group, a periodonaphthyl group, a nitronaphthyl group, a dinitronaphthyl group, a trinitronaphthyl group, etc.

An aryl group having the electron-withdrawing substituent in anion pertaining to the present invention, among the above-described specific example, is preferably the group represented by the general formula (XI), specifically, a trifluoromethylphenyl group, a nitrophenyl group, a dinitrophenyl group, a trinitrophenyl group, a monofluorophenyl group, a difluorophenyl group, a trifluorophenyl group, a perfluorophenyl group are preferable, and a difluorophenyl group, a trifluorophenyl group, a nitrophenyl group, a perfluorophenyl group are more preferable, and a nitrophenyl group, a perfluorophenyl group are further preferable.

Anion including an aryl group and anion group having the electron-withdrawing substituent pertaining to the present invention, specifically, includes, for example, the following general formula (XIII) to (XVI).

(XIII)

(wherein $R_{41}$, m are the same as the above-described one. m pieces of $R_{41}$ may be the same or different.)

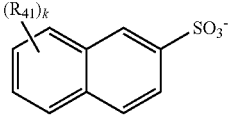
(XIV)

(wherein $R_{41}$, k are the same as the above-described one. k pieces of $R_{41}$ may be the same or different.)

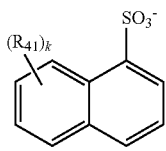

(XV)

(wherein $R_{41}$, k are the same as the above-described one. k pieces of $R_{41}$ may be the same or different.)

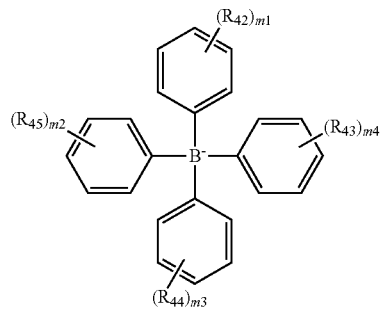

(XVI)

(wherein $R_{42}$ to $R_{45}$ each independently represent a halogenated alkyl group of 1 to 3 carbon atoms, a halogen or a nitro group, $m_1$ to $m_4$ each independently represent an integer of 1 to 5, $m_1$ pieces of $R_{42}$ may be same or different, and, $m_2$ pieces of $R_{43}$, $m_3$ pieces of $R_{44}$ and $m_4$ pieces of $R_{45}$ may also be same or different.).

Combination of $R_{41}$ and m in the general formula (XIII) includes, for example, the one described in the following table.

| $R_{41}$ | m |
|---|---|
| trifluoromethyl group (—CF$_3$) | 1 to 3 |
| perfluoroethyl group (—C$_2$F$_5$) | 1 to 3 |
| perfluoropropyl group (—C$_3$F$_7$) | 1 to 3 |
| fluorine atom | 1 to 5 |
| chlorine atom | 1 to 5 |
| bromine atom | 1 to 5 |
| iodine atom | 1 to 5 |
| nitro group | 1 to 3 |

The preferable specific example of anion represented by the general formula (XIII) includes, for example.

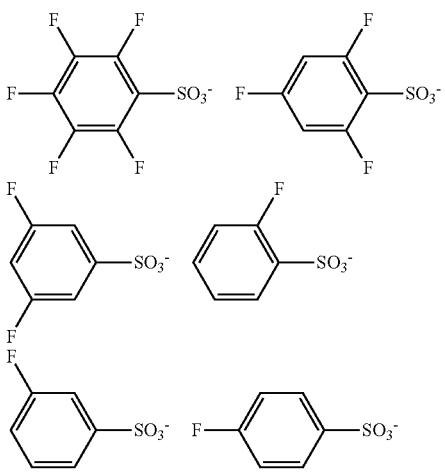

etc.

Combination of $R_{41}$ and m in the general formula (XIV) and (XV) includes, for example, the one described in the following table.

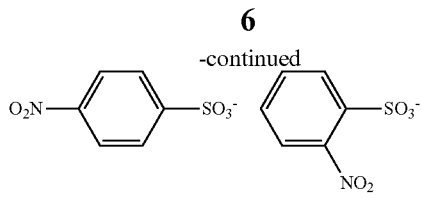
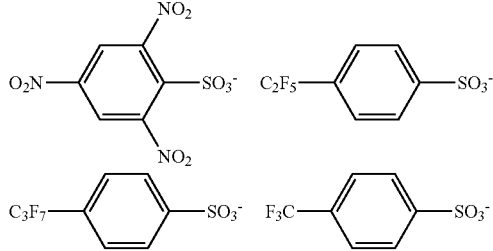

| $R_{41}$ | m |
|---|---|
| trifluoromethyl group (—CF$_3$) | 1 to 3 |
| perfluoroethyl group (—C$_2$F$_5$) | 1 to 3 |
| perfluoropropyl group (—C$_3$F$_7$) | 1 to 3 |
| nitro group | 1 to 4 |
| fluorine atom | 1 to 7 |
| chlorine atom | 1 to 7 |
| bromine atom | 1 to 7 |
| iodine atom | 1 to 7 |

The preferable specific example of anion represented by the general formula (XIV) and (XV) includes, for example,

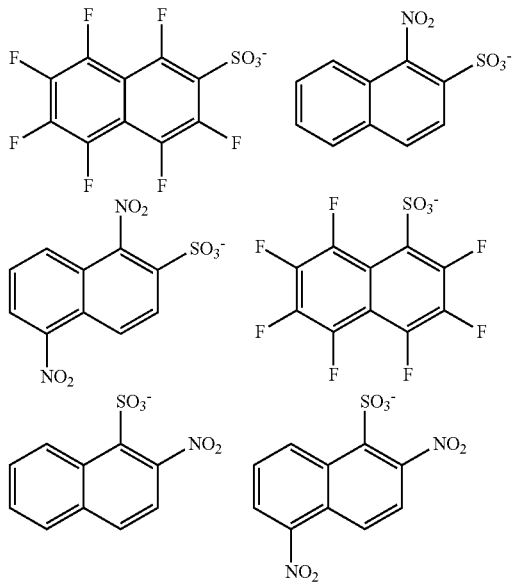

etc.

Combination of $R_{42}$ to $R_{45}$ and $m_1$ to $m_4$ in the general formula (XVI) includes, for example, the one described in the following table.

| $R_{42}$ | $m_1$ | $R_{43}$ | $m_2$ | $R_{44}$ | $m_3$ | $R_{45}$ | $m_4$ |
|---|---|---|---|---|---|---|---|
| —CF$_3$ | 1 to 3 | —CF$_3$ | 1 to 3 | —CF$_3$ | 1 to 3 | —CF$_3$ | 1 to 3 |
| —C$_2$F$_5$ | 1 to 3 | —C$_2$F$_5$ | 1 to 3 | —C$_2$F$_5$ | 1 to 3 | —C$_2$F$_5$ | 1 to 3 |

| $R_{42}$ | $m_1$ | $R_{43}$ | $m_2$ | $R_{44}$ | $m_3$ | $R_{45}$ | $m_4$ |
|---|---|---|---|---|---|---|---|
| —$C_3F_7$ | 1 to 3 | —$C_3F_7$ | 1 to 3 | —$C_3F_7$ | 1 to 3 | —$C_3F_7$ | 1 to 3 |
| nitro group | 1 to 3 | nitro group | 1 to 3 | nitro group | 1 to 3 | nitro group | 1 to 3 |
| fluorine | 1 to 5 | fluorine | 1 to 5 | fluorine | 1 to 5 | fluorine | 1 to 5 |
| chlorine | 1 to 5 | chlorine | 1 to 5 | chlorine | 1 to 5 | chlorine | 1 to 5 |
| bromine | 1 to 5 | bromine | 1 to 5 | bromine | 1 to 5 | bromine | 1 to 5 |
| iodine | 1 to 5 | iodine | 1 to 5 | iodine | 1 to 5 | iodine | 1 to 5 |
| nitro group | 1 to 3 | fluorine | 1 to 5 | fluorine | 1 to 5 | fluorine | 1 to 5 |
| nitro group | 1 to 3 | nitro group | 1 to 3 | fluorine | 1 to 5 | fluorine | 1 to 5 |
| nitro group | 1 to 3 | nitro group | 1 to 3 | nitro group | 1 to 5 | fluorine | 1 to 5 |

The preferable specific example of anion represented by the general formula (XVI) includes, for example,

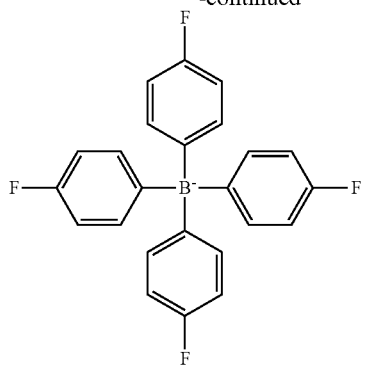

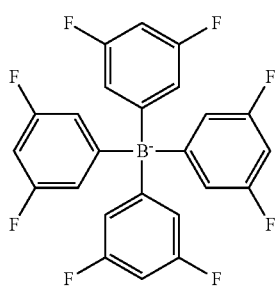

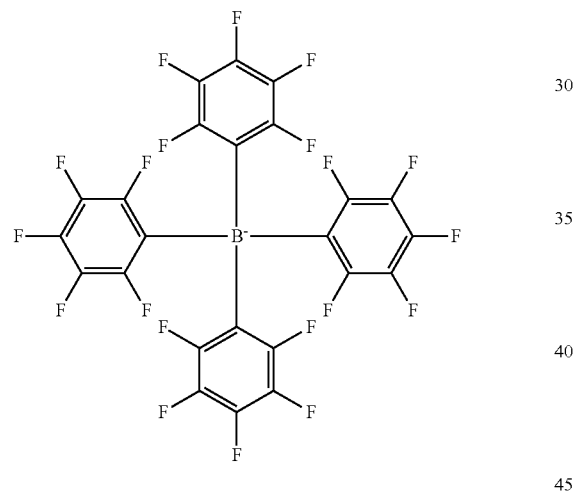

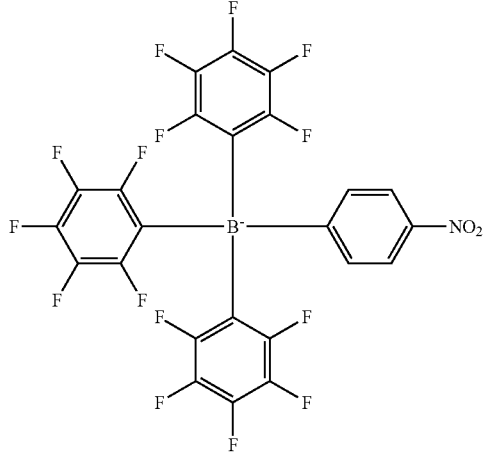

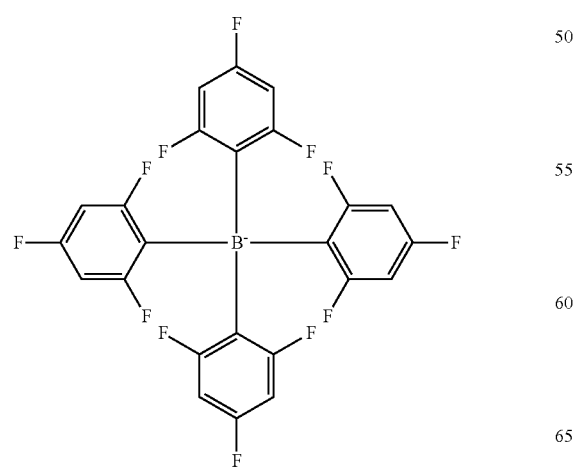

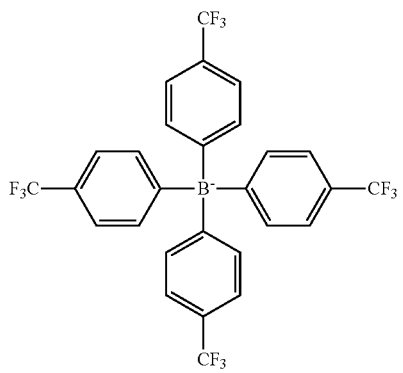

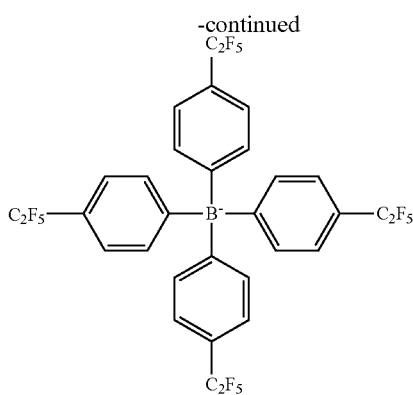
etc.,
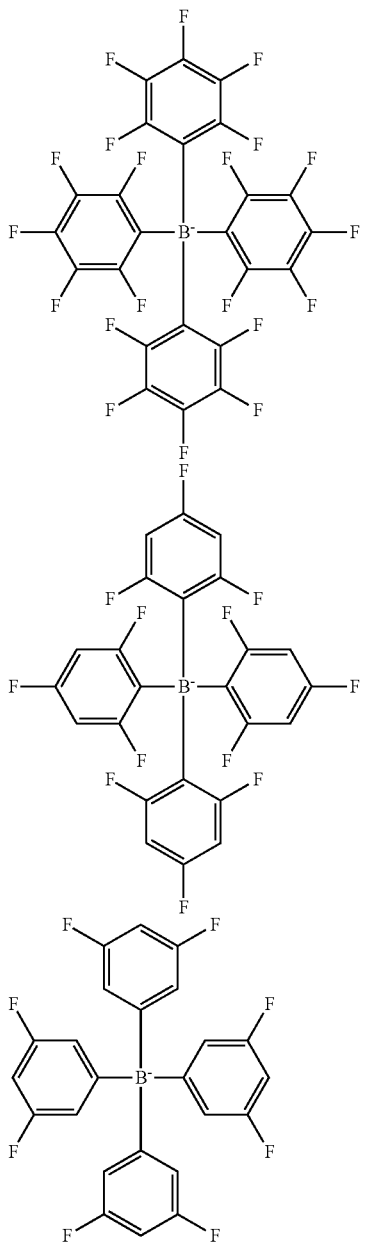
are preferable,
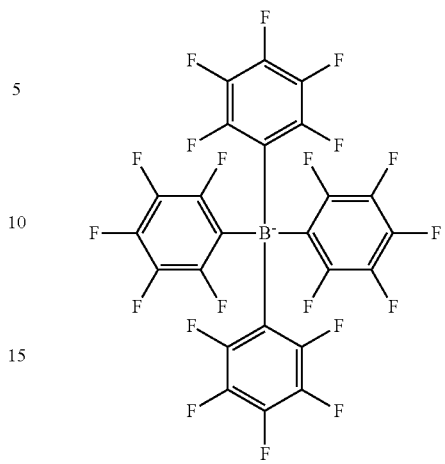
is more preferable.
Anion pertaining to the present invention is preferably the one represented by the general formula (XIII) or the general formula (XVI), and the one represented by the general formula (XVI) is more preferable. Among the above-described specific examples,
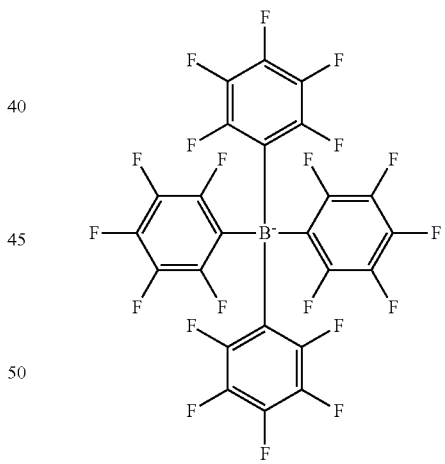
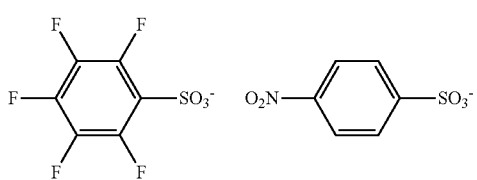
are particularly preferable,

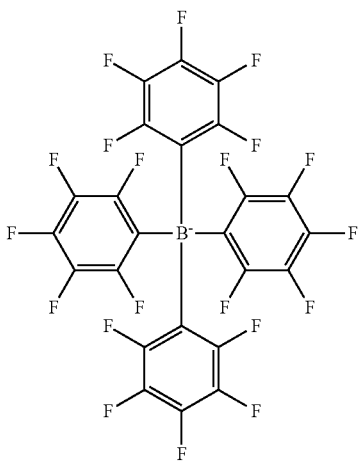 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

is further preferable.
[Cationic Rhodamine Derivative]

Cationic rhodamine derivative pertaining to the present invention is the one having anion pertaining to the above-described present invention, as a counter anion, and includes, for example, the compound represented by the following general formula (VII).

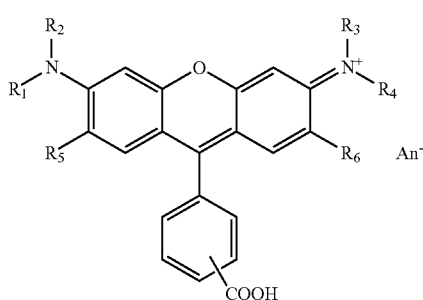

[wherein, $R_1$ to $R_4$ each independently represent a hydrogen atom; an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenalkyl group having 1 to 6 carbon atoms, a phenyl group or a benzyl group having a substituent or no substituent, and $R_5$ to $R_6$ each independently represent a hydrogen atom or a methyl group. An$^-$ represents anion (anion including an aryl group having the electron-withdrawing substituent and anion group) pertaining to the present invention.]

An alkyl group having 1 to 30 carbon atoms in the above-described $R_1$ to $R_4$ may be any of the straight chained, branched, or cyclic one, the one having 1 to 6 carbon atoms is preferable, the one having 1 to 3 carbon atoms is more preferable. Specifically, they include, for example, a methyl group, an ethyl group, a propyl group, an isopropyl group, a butyl group, a 1-methylpropyl group, an isobutyl group, a pentyl group, a 1-ethylpropyl group, a 1-methylbutyl group, a cyclopentyl group, a hexyl group, a 1-methylpentyl group, a 1-ethylbutyl group, a cyclohexyl group, a 2-heptyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an aralkyl group, an eicosyl group, a heneicosyl group, a docosyl group, a tricosyl group, a tetracosyl group, a pentacosyl group, a hexacosyl group, a heptacosyl group, an octacosyl group, a nonacosyl group, a triacontyl group, an isoheptyl group, an isooctyl group, an isononyl group, an isodecyl group, an isoundecyl group, an isododecyl group, an isotridecyl group, an isotetradecyl group, an isopentadecyl group, an isohexadecyl group, an isoheptadecyl group, an isooctadecyl group, an isononadecyl group, an isoaralkyl group, an isoeicosyl group, an isoheneicosyl group, an isodocosyl group, an isotricosyl group, an isotetracosyl group, an isopentacosyl group, an isohexacosyl group, an isoheptacosyl group, an isooctacosyl group, an isononacosyl group, an isotriacontyl group, a 1-methylhexyl group, a 1-ethylheptyl group, a 1-methylheptyl group, a 1-cyclohexylethyl group, a 1-heptyloctyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-t-butylcyclohexyl group, a 2-ethylhexyl group, a 1-adamantyl group, a 2-adamantyl group, etc. A methyl group, an ethyl group, a propyl group, an isopropyl group, a butyl group, a pentyl group, a hexyl group, etc, are preferable; and a methyl group, an ethyl group, a propyl group, etc. are more preferable.

A hydroxyalkyl group having 1 to 6 carbon atoms in the above-described $R_1$ to $R_4$ is preferably the one having 1 to 3 carbon atoms, specifically includes, for example, a hydroxymethyl group, a hydroxyethyl group, a hydroxypropyl group, a hydroxybutyl group, a hydroxypentyl group, a hydroxyhexyl group, etc.

A sulfoalkyl group having 1 to 6 carbon atoms in the above-described $R_1$ to $R_4$ is preferably the one having 1 to 3 carbon atoms, specifically includes, for example, a sulfomethyl group, a sulfoethyl group, a sulfopropyl group, a sulfobutyl group, a sulfopentyl group, sulfohexyl group, etc.

A carboxyalkyl group having 2 to 7 carbon atoms in the above-described $R_1$ to $R_4$ is preferably the one having 3 to 6 carbon atoms, specifically includes, for example, a carboxymethyl group, a carboxyethyl group, a carboxypropyl group, a carboxybutyl group, a carboxypentyl group, a carboxyhexyl group, etc., and a carboxyethyl group is preferable.

A cyanoalkyl group having 2 to 7 carbon atoms in the above-described $R_1$ to $R_4$ is preferably the one having 2 to 4 carbon atoms, specifically includes, for example, a cyanomethyl group, a cyanoethyl group, a cyanopropyl group, a cyanobutyl group, a cyanopentyl group, a cyanohexyl group, etc, a cyanoethyl group is preferable.

An alkoxyalkyl group having 2 to 6 carbon atoms in the above-described $R_1$ to $R_4$ is preferably the one having 3 to 5 carbon atoms, specifically includes, for example, a methoxymethyl group, a methoxyethyl group, an ethoxymethyl group, an ethoxyethyl group, a propoxymethyl group, a propoxyethyl group, a butoxymethyl group, a butoxyethyl group, etc.

A halogenalkyl group having 1 to 6 carbon atoms in the above-described $R_1$ to $R_4$ is preferably the one having 1 to 3 carbon atoms, specifically includes, for example, a trifluoromethyl group, a pentafluoroethyl group, a heptafluoropropyl group, a trichloromethyl group, a tribromomethyl group, a triiodomethyl group, etc.

A phenyl group or a benzyl group in the above-described $R_1$ to $R_4$ may have 1 to 5, preferably 1 to 3 substituents, and substituent thereof includes, for example, an alkyl group having 1 to 6 carbon atoms, such as a methyl group, an ethyl group, a propyl group, an isopropyl group, a butyl group, an isobutyl group, a t-butyl group, a pentyl group; a halogen atom, such as a fluorine atom, a chlorine atom, a bromine atom, a iodine atom; a sulfonic acid group; alkoxy group having 1 to 6 carbon atoms, such as a methoxy group, an ethoxy group, a propoxy group, a butoxy group, a t-butoxy group, a hexyloxy group; a hydroxyalkyl group, such as a hydroxyethyl group, a hydroxypropyl group; an alkoxyalkyl group having 2 to 10 carbon atoms, such as a methoxyethyl group, an ethoxyethyl group, an ethoxypropyl group, a butoxyethyl group; a hydroxyalkoxy group having 1 to 6 carbon atoms, such as 2-hydroxyethoxy group; an alkoxyalkoxy group having 2 to 10 carbon atoms, such as 2-methoxyethoxy group, a 2-ethoxyethoxy group; a sulfoalkyl group having 1 to 6 carbon atoms, such as 2-sulfoethyl group; a carboxyalkyl group having 2 to 7 carbon atoms, such as a carboxymethyl group, a carboxyethyl group, a carboxypropyl group, a carboxybutyl group, a carboxypentyl group, a carboxyhexyl group; a cyanoalkyl group having 2 to 7 carbon atoms, such as a cyanomethyl group, a cyanoethyl group, a cyanopropyl group, a cyanobutyl group, a cyanopentyl group, a cyanohexyl group, etc.

Among the specific example of the above-described $R_1$ to $R_4$, a hydrogen atom, a methyl group, an ethyl group, a propyl group, an isopropyl group, a butyl group, a pentyl group, a hexyl group, etc. are preferable, and a hydrogen atom, a methyl group, an ethyl group, a propyl group, etc, are more preferable, and a hydrogen atom, an ethyl group are particularly preferable.

The above-described $R_5$ and $R_6$ are preferably a hydrogen atom or a methyl group, Preferable combination of the above-described $R_1$ to $R_6$ includes, for example, the one described in the following table.

| $R_1$ | $R_2$ | $R_3$ | $R_4$ | $R_5$ | $R_6$ |
|---|---|---|---|---|---|
| ethyl group | ethyl group | ethyl group | ethyl group | hydrogen atom | hydrogen atom |
| methyl group | methyl group | methyl group | methyl group | hydrogen atom | hydrogen atom |
| methyl group | ethyl group | methyl group | ethyl group | hydrogen atom | hydrogen atom |
| hydrogen atom | methyl group | hydrogen atom | methyl group | hydrogen atom | hydrogen atom |
| hydrogen atom | ethyl group | hydrogen atom | ethyl group | hydrogen atom | hydrogen atom |
| ethyl group | ethyl group | ethyl group | ethyl group | methyl group | methyl group |
| methyl group | methyl group | methyl group | methyl group | methyl group | methyl group |
| methyl group | ethyl group | methyl group | ethyl group | methyl group | methyl group |
| hydrogen atom | methyl group | hydrogen atom | methyl group | methyl group | methyl group |
| hydrogen atom | ethyl group | hydrogen atom | ethyl group | methyl group | methyl group |

An⁻ includes the one described in the above paragraph [anion including an aryl group having the electron-withdrawing substituent and anion group], the preferable one is the same as the one described above.

[Polymer of the Present Invention]

Polymer of the present invention is the polymer having a monomer unit derived from the compound having the cationic rhodamine derivative pertaining to the above-described present invention and the ethylenically unsaturated bond pertaining to the present invention.

Weight average molecular weight (Mw) of the present invention is usually 2,000 to 100,000, preferably 2,000 to 50,000, more preferably 2,000 to 30,000. In addition, degree of dispersion thereof (Mw/Mn) is usually 1.00 to 5.00, preferably, 1.00 to 3.00.

Ethylenically unsaturated bond pertaining to the present invention may be polymerizable ethylenically unsaturated bond, and includes, specifically, a vinyl group etc. having no aromaticity. The group having such a ethylenically unsaturated bond includes an acryl group [$CH_2$=CH—C(=O)—], a methacryl group [$CH_2$=C($CH_3$)—C(=O)—], acrylamide group [$CH_2$=CH—C(=O)—NH—], methacrylamide group [$CH_2$=C($CH_3$)—C(=O)—NH—], etc.

The group having ethylenically unsaturated bond pertaining to the present invention and the cationic rhodamine derivative pertaining to the present invention are directly or bonded via suitable spacer. Said spacer includes, for example, an alkylene group having 1 to 21 carbon atoms which has at least one group of —O—, —OCO—, —COO— and an arylene group in a chain, and also a hydroxy group as a substituent: an alkylene group having 1 to 21 carbon atoms which has at least one group of —O—, —OCO—, —COO— and an arylene group in a chain; an alkylene group having 1 to 9 carbon atoms; or an alkylene group having 1 to 6 carbon atoms which has a hydroxy group as a substituent; etc., specifically includes, for example, the group described in $A_1$ in the following general formula (I) to be described later, etc.

Polymer of the present invention, specifically, includes the one having a monomer unit derived from the compound represented by the following general formula (I).

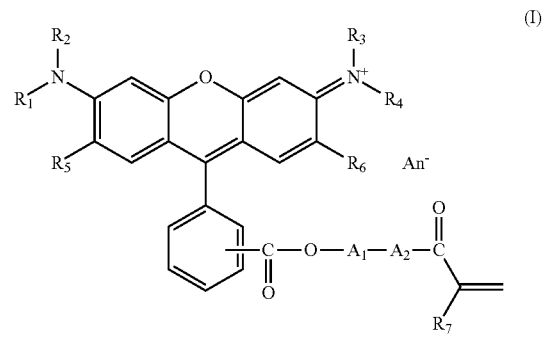

(wherein, $R_1$ to $R_6$ and An are the same as the above-described one. $R_7$ represents a hydrogen atom or a methyl group, $A_1$ represents an alkylene group having 1 to 21 carbon atoms which has at least one group of —O—, —OCO—, —COO— and an arylene group in a chain, and also a hydroxy group as a substituent; an alkylene group having 1 to 21 carbon atoms which has at least one group of —O—, —OCO—, —COO— and an arylene group in a chain; an alkylene group having 1 to 9 carbon atoms; or an alkylene group having 1 to 6 carbon atoms which has a hydroxy group as a substituent. $A_2$ represents —NH— or —O—.)

The above-described $R_7$ is preferably a methyl group,

An alkylene group having 1 to 9 carbon atoms in the above-described $A_1$ may be any of the straight-chained, branched, or cyclic one, and the one having 1 to 6 carbon atoms is preferable, the one having 1 to 3 carbon atoms is more preferable. Specifically, they include, for example, a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group, a n-heptylene group, a n-octylene group, a n-nonylene group, a methylenecyclohexylmethyl group, etc. A methylene group, an ethylene group, a propylene group, a butylene group, a pentylene group, a hexylene group, etc. are preferable, a methylene group, an ethylene group, a propylene group are more preferable, and an ethylene group is particularly preferable.

An alkylene group having 1 to 6 carbon atoms which has a hydroxy group as a substituent, in the above-described $A_1$ is preferably the one having 1 to 3 carbon atoms, specifically, they include, for example, a hydroxymethylene group, a hydroxyethylene group, a 1-hydroxypropylene group, a 2-hydroxypropylene group, a 1-hydroxybutylene group, a 1-hydroxypentylene group, a methylenehydroxyhexylmethyl group, etc.

An arylene group in an alkylene group having 1 to 21 carbon atoms which has —O—, —OCO—, —COO— group or arylene in a chain thereof, and also a hydroxy group as a substituent, in the above-described $A_1$ includes the one having 6 to 10 carbon atoms, specifically, includes a phenylene group, a naphthylene group, etc.

An alkylene group having 1 to 21 carbon atoms which contains —O—, —OCO—, —COO— group or arylene in a chain thereof, and also a hydroxy group as a substituent, in the above-described $A_1$ includes, for example, the group represented by the following general formula (VI-I)

$$—R_{51}—(CH_2)_{p1}— \quad (VI\text{-}I)$$

(wherein, $R_{51}$ represents a cycloalkylene group having 4 to 7 carbon atoms which has a hydroxy group as a substituent, p1 represents an integer of 1 to 3.), the group represented by the following general formula (VI-II) the group represented by $$—R_{52}—O—(CH_2)_{p2}— \quad (VI\text{-}II)$$

(wherein, $R_{52}$ represents an alkylene group having 1 to 6 carbon atoms which has a hydroxy group as a substituent, p2 represents an integer of 1 to 3.) etc.

A cycloalkylene group having 4 to 7 carbon atoms which has a hydroxy group as a substituent, in $R_{51}$ of the above-described general formula (VI-I) includes a hydroxycyclobutylene group, a hydroxycyclopentylene group, a hydroxycyclohexylene group, a hydroxycycloheptylene group, etc.

An alkylene group having 1 to 6 carbon atoms which has a hydroxy group as a substituent, in $R_{52}$ of the above-described general formula (VI-II) includes a hydroxymethylene group, a hydroxyethylene group, a hydroxypropylene group, a hydroxybutylene group, a hydroxypentylene group, a hydroxyhexylene group, etc.

Preferable specific example of the group represented by the general formula (VI-I) includes, for example,
—C$_6$H$_9$(OH)—CH$_2$—.
—C$_6$H$_9$(OH)—C$_2$H$_5$—,
—C$_6$H$_9$(OH)—C$_3$H$_7$—,
etc.

Preferable specific example of the group represented by the general formula (VI-II) includes, for example,
—CH$_2$—CH(OH)—CH$_2$—O—(CH$_2$)$_2$—,
—CH$_2$—CH(OH)—CH$_2$—O—(CH$_2$)$_3$—,
—CH$_2$—CH(OH)—CH$_2$—O—(CH$_2$)$_4$—,
etc.

An arylene group of an alkylene group having 1 to 21 carbon atoms which has at least one group of —O—, —OCO—, —COO— and an arylene group in a chain, in the above-described $A_1$ includes the one having 6 to 10 carbon atoms, and specifically, a phenylene group, a naphthylene group, etc.

An alkylene group having 1 to 21 carbon atoms which has at least one group of —O—, —OCO—, —COO— and an arylene group in a chain, in the above-described $A_1$ includes, for example, the group represented by the following general formula (VII-I)

$$—(CH_2)_{p3}—OCO—R_{53}—COO—(CH_2)_{p4}— \quad (VII\text{-}I)$$

(wherein, $R_{53}$ represents a phenylene group, a cycloalkylene group, p3 and p4 each independently represent integers of 1 to 3.),
the group represented by the general formula (VII-II)

$$—(C_2H_4O)_{p5}—(CH_2)_{p6}— \quad (VII\text{-}II):$$

(wherein, p5 represents an integer of 1 to 9, p6 represents an integer of 1 to 3.), the group represented by the general formula (VII-III):

$$—(CH_2CH(CH_3)O)_{p7}—R_{54}— \quad (VII\text{-}III)$$

(wherein, p7 represents an integer of 1 to 9, and $R_{54}$ includes the branched type alkylene group having 1 to 3 carbon atoms, etc.) etc.

The branched type alkylene group having 1 to 3 carbon atoms represented by the above-described $R_{54}$ includes a methylmethylene group, a methylethylene group, a methylpropylene group, etc.

The group represented by the above-described general formula (VII-I) specifically includes, for example,
—CH$_2$CH$_2$—O—CO—C$_6$H$_4$—CO—O—CH$_2$CH$_2$—,
—CH$_2$CH$_2$—O—CO—C$_6$H$_{10}$—CO—O—CH$_2$CH$_2$—, etc.

The group represented by the above-described general formula (VII-II) specifically includes, for example,
—(CH$_2$CH$_2$O)—CH$_2$CH$_2$—, —(CH$_2$CH$_2$O)$_2$—CH$_2$CH$_2$—,
—(CH$_2$CH$_2$O)$_3$—CH$_2$CH$_2$—, —(CH$_2$CH$_2$O)$_4$—CH$_2$CH$_2$—,
—(CH$_2$CH$_2$O)$_5$—CH$_2$CH$_2$—, —(CH$_2$CH$_2$O)$_6$—CH$_2$CH$_2$—,
—(CH$_2$CH$_2$O)$_7$—CH$_2$CH$_2$—, —(CH$_2$CH$_2$O)$_8$—CH$_2$CH$_2$—,
—(CH$_2$CH$_2$O)$_9$—CH$_2$CH$_2$—, etc.

The group represented by the above-described general formula (VII-III) specifically includes, for example,
—(CH$_2$CH(CH$_3$)O)—CH$_2$CH(CH$_3$)—,
—(CH$_2$CH(CH$_3$)O)$_2$—CH$_2$CH(CH$_3$)—,
—(CH$_2$CH(CH$_3$)O)$_3$—CH$_2$CH(CH$_3$)—,
—(CH$_2$CH(CH$_3$)O)$_4$—CH$_2$CH(CH$_3$)—,
—(CH$_2$CH(CH$_3$)O)$_5$—CH$_2$CH(CH$_3$)—,
—(CH$_2$CH(CH$_3$)O)$_6$—CH$_2$CH(CH$_3$)—,
—(CH$_2$CH(CH$_3$)O)$_7$—CH$_2$CH(CH$_3$)—,
—(CH$_2$CH(CH$_3$)O)$_8$—CH$_2$CH(CH$_3$)—,
—(CH$_2$CH(CH$_3$)O)$_9$—CH$_2$CH(CH$_3$)—
—CH(CH$_3$)CH$_2$—O—CH$_2$CH(CH$_3$)—, etc.

Among the specific example of the above-described $A_1$, a methylene group, an ethylene group, a propylene group, a butylene group, a pentylene group, a hexylene group, etc, are preferable, a methylene group, an ethylene group, a propylene group are more preferable, and an ethylene group is particularly preferable.

The above-described $A_2$ is preferably —O—.

The more number of atom between double bond and benzene ring, in the compound represented by the general formula (I), that is, number of atom in the straight chained part represented by —C(=O)—O-$A_1$-$A_2$-C(=O)— have, the higher reaction rate can be obtained when the relevant compound is polymerized, and the better effect as the polymer of the present invention can be accomplished. However, when these numbers are more than 16, these effect of heat resistance gradually decreases. Therefore, the numbers of atom thereof are usually 5 to 20, preferably 6 to 16, more preferably 6 to 14, particularly preferably 10 to 14.

Preferable combination of $R_1$ to $R_7$, $A_1$ and $A_2$ in the general formula (I) includes, for example, the one described in the following table.

| R₁ | R₂ | R₃ | R₄ | R₅ | R₆ | R₇ | A₁ | A₂ |
|---|---|---|---|---|---|---|---|---|
| ethyl group | ethyl group | ethyl group | ethyl group | hydrogen atom | hydrogen atom | methyl group or hydrogen atom | ethylene group | oxygen atom |
| ethyl group | ethyl group | ethyl group | ethyl group | hydrogen atom | hydrogen atom | methyl group or hydrogen atom | propylene group | oxygen atom |
| ethyl group | ethyl group | ethyl group | ethyl group | hydrogen atom | hydrogen atom | methyl group or hydrogen atom | 1-methylpropylene group | oxygen atom |
| ethyl group | ethyl group | ethyl group | ethyl group | hydrogen atom | hydrogen atom | methyl group or hydrogen atom | methylethylene group | oxygen atom |
| ethyl group | ethyl group | ethyl group | ethyl group | hydrogen atom | hydrogen atom | methyl group or hydrogen atom | 2-hydroxy propylene group | oxygen atom |
| methyl group | methyl group | methyl group | methyl group | hydrogen atom | hydrogen atom | methyl group or hydrogen atom | ethylene group | oxygen atom |
| methyl group | methyl group | methyl group | methyl group | hydrogen atom | hydrogen atom | hydrogen atom or hydrogen atom | ethylene group | oxygen atom |
| methyl group | methyl group | methyl group | methyl group | hydrogen atom | hydrogen atom | methyl group or hydrogen atom | propylene group | oxygen atom |
| hydrogen atom | methyl group | hydrogen atom | methyl group | methyl group | methyl group | methyl group or hydrogen atom | ethylene group | oxygen atom |
| hydrogen atom | ethyl group | hydrogen atom | ethyl group | methyl group | methyl group | methyl group or hydrogen atom | ethylene group | oxygen atom |
| hydrogen atom | methyl group | hydrogen atom | methyl group | hydrogen atom | hydrogen atom | methyl group or hydrogen atom | ethylene group | oxygen atom |
| hydrogen atom | ethyl group | hydrogen atom | ethyl group | hydrogen atom | hydrogen atom | methyl group or hydrogen atom | ethylene group | oxygen atom |

The polymer of the present invention may be either a homo-polymer or a copolymer, if this is the one having a monomer unit derived from the compound represented by the above-described general formula (I), and copolymer having high effect of heat resistance is preferable.

Said copolymer, includes, for example, the one consisting of a monomer unit derived from the compound represented by the above-described general formula (I), and 1 or 2 kinds of monomer units derived from the compounds represented by the following general formula (II), the general formula (III), the general formula (IV) or the general formula (V).

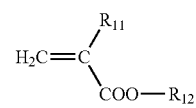
(II)

[wherein, $R_{11}$ represents a hydrogen atom or a methyl group, $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 10 carbon atoms which contains oxygen atom or no oxygen atom, a dialkylaminoalkyl group having 3 to 9 carbon atoms, a fluoroalkyl group having 1 to 18 carbon atoms, or an N-alkylenephthalimide group having 1 to 6 carbon atoms, the group represented by the following general formula (II-I):

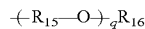
(II-I)

(wherein, $R_{15}$ represents an alkylene group having 1 to 3 carbon atoms, $R_{16}$ represents a phenyl group which has a hydroxy group as a substituent or no substituent, or an alkyl group having 1 to 3 carbon atoms, q represents an integer of 1 to 3.), the group represented by the following general formula (II-II)

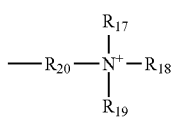
(II-II)

(wherein, $R_{17}$ to $R_{19}$ represents an alkyl group having 1 to 3 carbon atoms, $R_{20}$ represents an alkylene group having 1 to 3 carbon atoms)

the group represented by the following general formula (II-III)

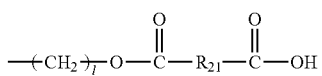
(II-III)

(wherein, l represents an integer of 1 to 6, $R_{21}$ represents a phenylene group or a cyclohexylene group.)],

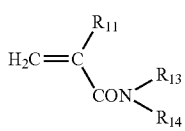
(III)

(wherein, $R_{11}$ is the same as the above-described one, $R_{13}$ represents a hydrogen atom or an alkyl group having 1 to 3 carbon atoms, $R_{14}$ represents a hydrogen atom or a dialkylaminoalkyl group having 3 to 7 carbon atoms, a hydroxyalkyl group having 1 to 6 carbon atoms; $R_{13}$ and $R_{14}$ may form a morpholino group together with nitrogen atom adjacent to this.),

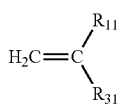

(IV)

(wherein, $R_{31}$ represents a phenyl group, a pyrrolidino group, $R_{11}$ is the same as the above-described one)

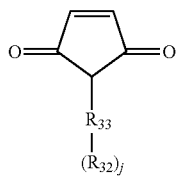

(V)

(wherein, $R_{33}$ represents a nitrogen atom or an oxygen atom, j represents 0 when $R_{33}$ is an oxygen atom, and represents 1 when $R_{33}$ is a nitrogen atom, $R_{32}$ represents a hydrogen atom: an alkyl group having 1 to 20 carbon atoms; a hydroxyalkyl group having 1 to 10 carbon atoms; a halogenated alkyl group having 1 to 10 carbon atoms; an alkylcycloalkyl group having 1 to 10 carbon atoms: a halogenated cycloalkyl group having 6 to 7 carbon atoms, an aryl group having 6 to 10 carbon atoms; an aryl group having 6 to 10 carbon atoms which contains an alkyl group having 1 to 6 carbon atoms as a substituent: or a halogenated aryl group having 6 to 10 carbon atoms.)

$R_{11}$ in the general formula (II) is preferably a methyl group.

An alkyl group having 1 to 18 carbon atoms in $R_{12}$ of the general formula (II) may be the straight chained, branched or cyclic one, includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a n-nonyl group, a n-decyl group, a n-undecyl group a n-dodecyl group, a n-tridecylgroup, a n-tetradecyl group, a n-pentadecyl group, a n-hexadecyl group, a n-heptadecyl group, a n-octadecyl group, a cyclopropyl group, a cyclopentyl group, a cyclohexyl group, a cycloheptyl group, a cyclooctyl group, a cyclodecyl group, a cycloundecyl group, a cyclododecyl group, a cyclotetradecyl group, cyclooctadecyl group, etc.

A hydroxyalkyl group having 1 to 10 carbon atoms in $R_{12}$ of the general formula (II) includes, for example, a hydroxyethyl group, a hydroxypropyl group, a hydroxybutyl group, a hydroxypentyl group, a hydroxyhexyl group, etc.

An aryl group having 6 to 10 carbon atoms in $R_{12}$ of the general formula (II) includes, a phenyl group, a naphthyl group, etc.

An arylalkyl group having 7 to 13 carbon atoms in $R_{12}$ of the general formula (II) includes a benzyl group, a phenylethyl group, a phenylpropyl group, a naphthylmethyl group, a naphthylethyl group, a naphthylpropyl group, etc., a benzyl group is preferable.

An alkoxyalkyl group having 2 to 9 carbon atoms in $R_{12}$ of the general formula (II) includes a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, a propoxymethyl group, a propoxyethyl group, a propoxypropyl group, a propoxybutyl group, a propoxypentyl group, a propoxyhexyl group, etc.

An alkoxyalkoxyalkyl group having 3 to 9 carbon atoms in $R_{12}$ of the general formula (II) includes a methoxymethoxymethyl group, a methoxymethoxyethyl group, a methoxymethoxypropyl group, an ethoxymethoxymethyl group, an ethoxymethoxyethyl group, an ethoxymethoxypropyl group, a propoxymethoxymethyl group, a propoxymethoxyethyl group, a propoxymethoxypropyl group, an ethoxyethoxymethyl group, an ethoxyethoxyethyl group, an ethoxyethoxypropyl group, an ethoxyethoxymethyl group, an ethoxyethoxyethyl group, an ethoxyethoxypropyl group, a propoxyethoxymethyl group, a propoxyethoxyethyl group, a propoxyethoxypropyl group, etc.

An aryloxyalkyl group having 7 to 13 carbon atoms in $R_{12}$ of the general formula (II) includes a phenoxymethyl group, a phenoxyethyl group, a phenoxypropyl group, a naphthyloxymethyl group, a naphthyloxyethyl group, a naphthyloxypropyl group, etc.

A morpholinoalkyl group having 5 to 7 carbon atoms in $R_{12}$ of the general formula (II) includes, for example, a morpholinomethyl group, a morpholinoethyl group, a morpholinopropyl group, etc.

A trialkylsilyl group having 3 to 9 carbon atoms in $R_{12}$ of the general formula (II) includes, for example, a trimethylsilyl group, a triethylsilyl group, a tripropylsilyl group, a dimethylethylsilyl group, a diethylmethylsilyl group, etc.

An alicyclic hydrocarbon group having 6 to 10 carbon atoms which has oxygen in $R_{12}$ of the general formula (II) includes a dicyclopentenyloxyethyl group, etc.

An alicyclic hydrocarbon group having 6 to 10 carbon atoms which has no-oxygen in $R_{12}$ of the general formula (II) includes a cyclohexyl group, an isobornyl group, and a dicyclopentadienyl group, etc.

A dialkylaminoalkyl group having 3 to 9 carbon atoms in $R_{12}$ of the general formula (II) includes a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, etc.

A fluoroalkyl group having 1 to 18 carbon atoms in $R_{12}$ of the general formula (II) includes a 2,2,2-trifluoroethyl group, a 2,2,3,3-tetrafluoropropyl group, a 2,2,3,3-tetrafluoropropyl group, a 2,2,3,3,4,4-hexafluoropropyl group, a 2,2,3,3,4,4,5,5-octafluoropentyl group, a 3,3,4,4,5,5,6,6,7,7,8,8,9,9,10,10,10-heptadecafluorodecyl; a 2-(heptadecafluorooctyl)ethyl group, etc.

An N-alkylenephthalimide group having 1 to 6 carbon atoms in $R_{12}$ of the general formula (II) includes a 2-phthalimideethyl group, a 2-tetrahydrophthalimideethyl group, etc.

An alkylene group having 1 to 3 carbon atoms in $R_{15}$ of the general formula (II-I) includes a methylene group, an ethylene group, and a propylene group, etc., and an ethylene group is preferable.

A phenyl group having a hydroxy group as a substituent or no substituent in $R_{16}$ of the general formula (II-I) includes a hydroxyphenyl group, a phenyl group, etc.

An alkyl group having 1 to 3 carbon atoms in $R_{16}$ of the general formula (II-I) includes a methyl group, an ethyl group, a propyl group, etc.

Specific example of the group represented by the general formula (II-I) includes a 2-hydroxy-3-phenoxymethyl group, a 2-hydroxy-3-phenoxyethyl group, a 2-hydroxy-3-phenoxypropyl group, a methyltrimethylene glycol group, a methyltriethylene glycol group, and a methyltripropylene glycol group, etc., among them, a 2-hydroxy-3-phenoxypropyl group, a methyltripropylene glycol group, and a methyltriethylene glycol group, etc. are preferable.

An alkyl group having 1 to 3 carbon atoms in $R_{17}$ to $R_{19}$ of the general formula (II-II) includes a methyl group, an ethyl group, a propyl group, etc., and a methyl group is preferable.

An alkylene group having 1 to 3 carbon atoms in $R_{20}$ to the general formula (II-II) includes a methylene group, an ethylene group, a propylene group, etc.

Specific example of the group represented by the general formula (II-II) includes a trimethylammoniummethyl group, a trimethylammoniumethyl group, a triethylammoniummethyl group, and a triethylammoniumethyl group, etc.

Preferable specific example of the group represented by the general formula (II-II) includes, for example,

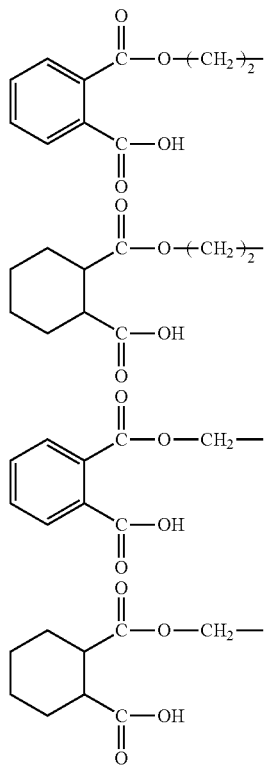

etc.

$R_{12}$ of the general formula (II), among the above-described group, is preferably a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an aryloxyalkyl group having 7 to 13 carbon atoms, the group represented by the general formula (II-I), and the group represented by the general formula (II-III), among them, a hydrogen atom, an arylalkyl group having 7 to 13 carbon atoms, and the group represented by the general formula (II-III) are more preferable.

Preferable specific example of the general formula (II) includes methacrylic acid, benzyl methacrylate, hydroxyethyl methacrylate, and methyl methacrylate, etc., among them, methacrylic acid, benzyl methacrylate, etc. are preferable.

An alkyl group having 1 to 3 carbon atoms in $R_{13}$ of the general formula (III) includes a methyl group, an ethyl group, and a propyl group, etc.

A dialkylaminoalkyl group having 3 to 9 carbon atoms in $R_{14}$ of the general formula (III) includes a dimethylaminomethyl group, a dimethylaminoethyl group, a dimethylaminopropyl group, a diethylaminomethyl group, diethylaminoethyl group, a diethylaminopropyl group, a dipropylaminomethyl group, a dipropylaminoethyl group, a dipropylaminopropyl group, etc. An alkyl group having 1 to 3 carbon atoms includes the same as the above-described $R_{13}$.

A hydroxyalkyl group having 1 to 6 carbon atoms in $R_{14}$ of the general formula (III) includes a hydroxymethyl group, an hydroxyethyl group, a hydroxypropyl group, a hydroxybutyl group, a hydroxypentyl group, and a hydroxyhexyl group, etc., and a hydroxyethyl group is preferable.

Preferable specific example of the general formula (III) includes (meth)acrylamide. N,N-dimethylacrylamide, N,N-diethylacrylamide, hydroxyethyl(meth)acrylamide, and 4-acryloyl morpholine, etc., among them, (meth)acrylamide, N,N-dimethylacrylamide, and N,N-diethylacrylamide are preferable, and N,N-diethylacrylamide is particularly preferable.

Preferable specific example of the general formula (IV) includes styrene, α-methylstyrene, and N-vinylpyrrolidone, etc., among them, styrene, α-methylstyrene are preferable, and styrene is particularly preferable.

An alkyl group having 1 to 20 carbon atoms in $R_{32}$ of the general formula (V) may be the straight chained, branched or cyclic one, includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a nonadecyl group, and an icosyl group, etc.

A hydroxyalkyl group having 1 to 10 carbon atoms in $R_{32}$ of the general formula (V) includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, and a hydroxydecyl group, etc.

A halogenated alkyl group having 1 to 10 carbon atoms in $R_{32}$ of the general formula (V) includes, for example, a chloromethyl group, a chloroethyl group, a chloro-n-propyl group, a chloroisopropyl group, a chloro-n-butyl group, a chloro-tert-butyl group, a chloro-n-pentyl group, a chloro-n-hexyl group, a chloro-n-heptyl group, a chloro-n-octyl group, a chloro-n-nonyl group, a chloro-n-decyl group, a fluoromethyl group, a fluoroethyl group, a fluoron-propyl group, a fluoroisopropyl group, a fluoro-n-butyl group, a fluoro-tert-butyl group, a fluoro-n-pentyl group, a fluoro-n-hexyl group, a fluoro-n-heptyl group, a fluoro-n-octyl group, a fluoro-n-nonyl group, and a fluoro-n-decyl group, etc.

An alkylcycloalkyl group having 1 to 10 carbon atoms in $R_{32}$ of the general formula (V) includes, for example, a methylcyclohexyl group, an ethylcyclohexyl group, a propylcyclohexyl group, and a butylcyclohexyl group, etc.

A halogenated cycloalkyl group having 6 to 7 carbon atoms in $R_{32}$ of the general formula (V) includes, a chlorocyclohexyl group, a fluorocyclohexyl group, a bromocyclohexyl group, a chlorocycloheptyl group, fluorocycloheptyl group, and a bromocycloheptyl group, etc.

An aryl group having 6 to 10 carbon atoms in $R_{32}$ of the general formula (V) includes a phenyl group, a naphthyl group, etc.

An aryl group having 6 to 10 carbon atoms which contains an alkyl group having 1 to 6 carbon atoms as a substituent in $R_{32}$ of the general formula (V), includes a methylphenyl group, an ethylphenyl group, a n-propylphenyl group, a n-butylphenyl group, a n-pentylphenyl group, and a n-hexylphenyl group, etc.

A halogenated aryl group having 6 to 10 carbon atoms in $R_{32}$ of the general formula (V) includes a chlorophenyl group, a fluorophenyl group, a chloronaphthyl group, and a fluoronaphthyl group, etc.

Preferable specific example of the general formula (V) includes maleic anhydride, maleimide, N-methylmaleimide. N-ethylmaleimide, N-butylmaleimide, N-octylmaleimide, N-dodecylmaleimide, N-(2-ethylhexyl)maleimide, N-(2-hydroxyethyl)maleimide, N-(2-chlorohexyl)maleimide, N-cyclohexylmaleimide, N-(2-methylcyclohexyl)maleimide. N-(2-ethylcyclohexyl)maleimide. N-(2-chlorocyclohexyl)maleimide, N-phenylmaleimide, N-(2-methylphenyl)maleimide, and N-(2-ethylphenyl)maleimide, N-(2-chlorophenyl)maleimide, etc., among them. N-phenylmaleimide is preferable.

Copolymer of the present invention specifically includes combination of the following monomer unit, among them, combination 1, 5, 6 and 7 is preferable, in combination 1, the one having 2 kinds of the compounds represented by the general formula (II) is preferable.

| | compound derived from monomer unit | | |
|---|---|---|---|
| combination 1 | general formula (I) | general formula (II) | |
| combination 2 | general formula (I) | general formula (III) | |
| combination 3 | general formula (I) | general formula (IV) | |
| combination 4 | general formula (I) | general formula (V) | |
| combination 5 | general formula (I) | general formula (II) | general formula (III) |
| combination 6 | general formula (I) | general formula (II) | general formula (IV) |
| combination 7 | general formula (I) | general formula (II) | general formula (V) |

Weight ratio of monomer unit derived from the compound represented by the general formula (I) and a monomer unit derived from the compound represented by the general formula (II), the general formula (III), the general formula (IV), or the general formula (V) may be appropriately set according to the type of monomer unit to be used, but a monomer unit derived from the compound represented by the general formula (I) to total weight of the obtained polymer is usually 1 to 90% by weight, preferably 5 to 85% by weight.

[Production Method of Polymer of the Present Invention]

Polymer of the present invention is produced, for example, as follows. That is, polymer of the present invention can be obtained by subjecting the compound of the present invention obtained as described above to the polymerization reaction known per se. When polymer of the present invention is a copolymer, in polymerization reaction, after mixing the above-described compound of the present invention with 1 or 2 kinds of the compounds represented by the general formula (II), the general formula (III), the general formula (IV) or the general formula (V) so that ratio monomer unit derived from each monomer in the finally obtained polymer is as described above, polymerization may be carried out.

The above-described polymerization reaction is carried out, for example, as follows. That is, the compound represented by the general formula (I) having anion pertaining to the present invention, or the compound represented by the general formula (I) having anion pertaining to the present invention and 1 or 2 kinds of compounds represented by the general formula (II), the general formula (III), the general formula (IV) or the general formula (V) were dissolved in the appropriate solvent of 1 to 10 times volume to total volume thereof, for example, toluene, 1,4-dioxane, tetrahydrofuran, isopropanol, methyl ethyl ketone, propylene glycol monomethyl ether acetate, etc., and then, under the existence of 0.01 to 30% by weight of polymerization initiator, for example, azoisobutyronitrile, 2,2'-azobis(2,4-dimethylvaleronitrile), 2,2'-azobis(2-methylpropionate), 2,2'-azobis(2-methylbutyronitrile), benzoylperoxide, lauroyl peroxide, etc., to the total volume of the dissolved compound for, reaction was carried out at 50 to 150° C. for 1 to 48 hours. After reaction, treatment may be carried out according to the conventional method of polymer acquisition.

[Compound of the Present Invention]

The compound of the present invention is the one having cationic rhodamine derivative pertaining to the above-described present invention, and ethylenically unsaturated bond pertaining to the above-described present invention and also anion pertaining to the above-described present invention as counter anion.

The compound of the present invention specifically includes, for example, the compound represented by the above-described general formula (I). Specific example, preferable one, preferable combination of $R_1$ to $R_7$, $A_1$, $A_2$, and $An^-$ in the general formula (I) includes the same as the one described in the paragraph of the above-described [Polymer of the present invention]

[Production Method of Compound of the Present Invention]

The compound of the present invention is, for example, produced as follows.

That is, firstly, a rhodamine compound represented by the following general formula (I-I):

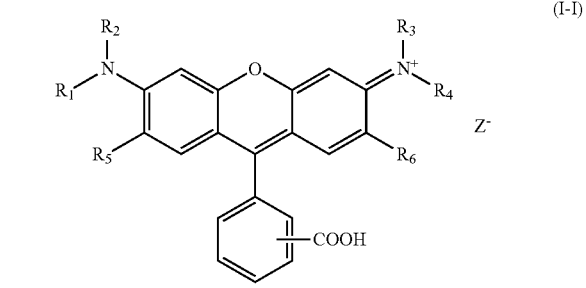

(wherein, $R_1$ to $R_6$ are the same as the above-described one, $Z^-$ represents anion.), and the compound represented by the following general formula (I-II):

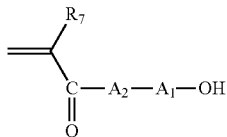

(I-II)

(wherein, $R_7$, $A_1$ and $A_2$ are the same as the above-described one.)
are reacted under existence of dehydrated condensing agent to obtain the compound represented by the following general formula (I-III),

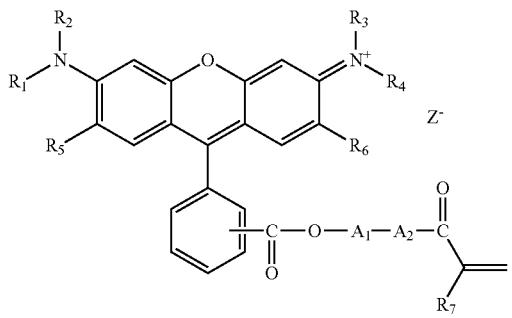

(I-III)

(wherein, $R_1$ to $R_7$, $A_1$, $A_2$ and $Z^-$ are the same as the above-described one.) The compound represented by the general formula (I-III), as the another method, may be obtained by reacting, rhodamine derivative represented by the general formula (I-I), under existence of catalyst, with the compound represented by the general formula (I-IV).

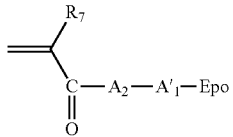

(I-IV)

(wherein, $R_7$ and $A_2$ are the same as the above-described one. $A'_1$ represents an alkylene group having 1 to 21 carbon atoms which has at least one group of —O— and an arylene group in a chain, an alkylene group having 1 to 9 carbon atoms, Epo represents a 3,4-epoxycyclohexyl or an epoxy group,).

After obtaining the compound of the general formula (I-III), if needed (in the case when $Z^-$ is the one other than anion pertaining to the present invention), it is possible to obtain the compound of the present invention according to carrying out ion-exchange reaction of anion by contacting the salt (for example, sodium salt, potassium salt, lithium salt, etc. of said anion) of anion which includes an aryl group having the electron-withdrawing substituent pertaining to the present invention with the compound represented by the general formula (I-III) in the suitable solvent, such as dichloromethane, for example, for 10 to 120 minutes at 10 to 50° C.

Anion represented by $Z^-$ in the general formula (I-I) and the general formula (I-III) includes $Cl^-$, $NO_3^-$, $SO_4^-$, $PO_4^-$, etc., and it may be the compound including them, or may be anion pertaining to the present invention.

The preferable combination of $R_1$ to $R_6$ in the above-described general formula (I-I) includes the same one as the combination described in the paragraph of the above-described general formula (I).

The preferable combination of $R_7$, $A_1$ and $A_2$ in the above-described general formula (I-II) includes the same one as the combination described in the paragraph of the above-described general formula (I). Used amount of the compound represented by the general formula (I-II) in the reaction to obtain the compound represented by the above-described general formula (I-III) is 1 to 5 times mole, preferably 1 to 2 times mole of the rhodamine derivative represented by the general formula (I-I).

The above-described dehydration condensing agent may be, for example, the one generally used as the dehydration condensing agent, includes, for example, inorganic dehydrating agents, such as diphosphorus pentaoxide, anhydrous zinc chloride; for example, carbodiimides, such as dicyclohexylcarbodiimide, diisopropylcarbodiimide, 1-ethyl-3-(3-dimethylaminopropylcarbodiimide) hydrochloride; for example, polyphosphoric acid, acetic anhydride, sulfuric acid, carbonyldiimidazole, p-toluenesulfonic acid, etc., and carbodiimides are preferable. Used amount of said dehydration condensing agent is 1 to 10 times mole, preferably 1 to 5 times mole to the compound represented by the general formula (I-II). In the reaction to obtain the compound represented by the above-described general formula (I-III), catalyst, such as dimethylaminopyridine may be used to improve efficiency of the dehydration condensing agent. Used amount of said catalyst is 0.1 to 10 times mole to the compound represented by the general formula (I-II).

The reaction to obtain the compound represented by the above-described general formula (I-III) is usually carried out by reacting in reaction solvent at 10 to 50° C. for 5 to 24 hours. Said reaction solvent includes, for example, ethers, such as diethyl ether, diisopropyl ether, a ethylmethyl ether, tetrahydrofuran, 1,4-dioxane, and dimethoxyethane: for example, ketones, such as acetone, dimethyl ketone, methyl ethyl ketone, diethyl ketone, 2-hexanone, t-butyl methyl ketone, cyclopentanone, cyclohexanone; for example, halogenated hydrocarbons, such as chloromethane, methylene chloride, chloroform, dichloromethane, dichloroethane, trichloroethane, chlorobenzene; for example, hydrocarbons, such as n-hexane, benzene, toluene, xylene; for example, esters, such as ethyl acetate, butyl acetate, methyl propionate; for example, nitriles, such as acetonitrile; for example, amides, such as N,N-dimethylformamide; etc., among them, halogenated hydrocarbons are preferable, dichloromethane is more preferable. These may be used alone or in combination of two or more kinds appropriately. Used amount of the reaction solvent is usually 1 to 50 times mole, preferably 1 to 20 times mole to the total amount of rhodamine derivative represented by the general formula (I-I) and the compound represented by the general formula (I-II).

An alkylene group having 1 to 21 carbon atoms which has at least one group of —O— and an arylene group in a chain, in $A'_1$ of the compound represented by the above-described general formula (I-IV) includes the same as an alkylene group having 1 to 21 carbon atoms which has at least one group of —O— and an arylene group in the above-described $A'_1$ in a chain.

An alkylene group having 1 to 9 carbon atoms in A'$_1$ in the compound represented by the above-described general formula (I-IV) includes the same as an alkylene group having 1 to 9 carbon atoms in the above-described A$_1$.

Preferable combination of R$_7$, A'$_1$ and A$_2$ in the above-described general formula (I-IV) includes the combination in accordance with the preferable one of R$_7$, A$_1$ and A$_2$ described in the paragraph of the above-described general formula (I). Used amount of the compound represented by the general formula (I-IV) is 1 to 5 times mole, preferably 1 to 2 times mole of rhodamine derivative represented by the general formula (I-I).

Catalyst used in the method to obtain the the compound of the general formula (I-III) by using the compound represented by the above-described general formula (I-IV) includes, for example, quaternary salt catalyst, such as tetraethylammonium bromide, tetrabutylammonium bromide, tetraethylammonium chloride, tetrabutylphosphonium bromide, triphenylbenzylphosphonium chloride; amines, such as triethylamine, tributylamine; etc. Used amount of said catalyst is 1 to 10 times mole, preferably 1 to 5 times mole to the compound represented by the general formula (I-I).

The method to obtain the compound of the general formula (I-III) by using the compound represented by the above-described general formula (I-IV) is usually carried out by reacting in the reaction solvent at 10 to 50° C. for 5 to 24 hours. Said reaction solvent includes the same as the one described in the method to obtain the compound of above-described general formula (I-III). These may be used alone or in combination of two or more kinds appropriately. Used amount of the reaction solvent is usually 1 to 50 times volume, preferably 1 to 20 times volume to total volume of rhodamine derivative represented by the general formula (I-I) and the compound represented by the general formula (I-III).

[Colored Composition]

The colored composition of the present invention is the one including at least one kind of the polymer and the compound of the above-described present invention. Because said colored composition can form the excellent colored cured film, it can be used in the application of colored pixel formation, such as color filter used in a liquid crystal display (LCD) or a solid-state imaging device (CCD, CMOS, etc,), or in the application of printing ink, inkjet ink, and paint etc. Particularly, it can be suitably used for the color filter of liquid crystal display.

The colored composition of the present invention is preferably the one including at least one kind of the polymer or the compound of the above-described present invention, polymerization initiator, binder resin, and radical polymerizing monomer or oligomer, if necessary, pigment, solvent, silane coupling agent and cross-linking agent, etc, may be included. Said colored composition contains 1 to 50%, preferably 5 to 30% of the polymer or the compound of the present invention to the weight of the colored composition. In addition, weight of the colored composition herein means weight of solid component except solvent, and represents the same meaning in the following present application.

As the above-described polymerization initiator, known thermal polymerization initiator, light polymerization initiator can be used, and light polymerization initiator is preferable. Specifically, they include acetophenone type, such as diethoxyacetophenone, 2-hydroxy-2-methyl-1-phenylpropane-1-one, benzyldimethylketal, 1-(4-isopropylphenyl)-2-hydroxy-2-methylpropane-1-one, 4-(2-hydroxyethoxy)phenyl (2-hydroxy-2-propyl)ketone, 1-hydroxycyclohexyl phenyl ketone, 2-methyl-2-morpholino(4-thiomethylphenyl)propane-1-one, 2-benzyl-2-dimethylamino-1-(4-morpholinophenyl)-butanone; benzoin type, such as benzoin, benzoin isopropyl ether, benzoin isobutyl ether; acylphosphine oxide type, such as 2,4,6-trimethylbenzoyldiphenylphosphine oxide; benzyl, methylphenylglyoxy ester type: benzophenone type, such as benzophenone, methyl o-benzoylbenzoate, 4-phenylbenzophenone, 4,4'-dichlorobenzophenone, hydroxybenzophenone, 4-benzoyl-4'-methyldiphenyl sulfide, acrylated benzophenone, 3,3',4,4'-tetra(t-butylperoxycarbonyl)benzophenone, 3,3'-dimethyl-4-methoxybenzophenone; thioxanthone type, such as 2-isopropylthioxanthone, 2,4-dimethylthioxanthone, 2,4-diethylthioxanthone, 2,4-dichlorothioxanthone; aminobenzophenone type, such as Michler's ketone, 4,4'-diethylaminobenzophenone; oxime ester type, such as 1-[4-(phenylthio)phenyl]-1,2-octanedione 2-(o-benzoyloxime), 1-[6-(2-methylbenzoyl)-9-ethyl-9H-carbazol-3-yl]ethanone o-acetyloxime; 10-butyl-2-chloroacridine, 2-ethylanthraquinone, 9,10-phenanthrene quinone, camphor quinone, etc.

The above-described polymerization initiator may be alone, or contain 2 or more kinds. Content thereof is 1 to 50% by weight, preferably 5 to 30% by weight to the weight of the colored composition.

The above-described binder resin includes, for example, ethylenically unsaturated monomer having at least one of a carboxyl group or a hydroxy group, or copolymer of said ethylenically unsaturated monomer and ethylenically unsaturated monomer having an aromatic hydrocarbon group or an aliphatic hydrocarbon group, the one having an epoxy group in a side chain or terminal, etc., of said copolymer, and the one in which acrylate was added, etc. These may be used alone, or in combination of 2 or more kinds.

Specific example of the above-described ethylenically unsaturated monomer having a carboxyl group includes unsaturated mono carboxylic acids, such as acrylic acid, methacrylic acid, benzyl methacrylate, crotonic acid, α-chloroacrylic acid, ethacrylic acid, cinnamic acid; unsaturated dicarboxylic acids (anhydride), such as maleic acid, maleic anhydride, fumaric acid, itaconic acid, itaconic anhydride, citraconic acid, citraconic anhydride, mesaconic acid; 3 or more polyvalent unsaturated carboxylic acids (anhydrides), 2-(meth)acryloyloxyethyl hexahydrophthalate, 2-methacryloyloxyethyl 2-hydroxypropyl phthalate, 2-acryloyloxyethyl 2-hydroxyethyl phthalate, etc.

Content of the above-described binder resin is 10% by weight to 50% by weight, preferably 20% by weight to 50% by weight to the weight of the colored composition.

The above-described radical polymerizable monomer or oligomer includes, as one example, polyethylene glycol diacrylate (the one having 2 to 14 numbers of ethylene group), polyethylene glycol dimethacrylate (the one having 2 to 14 numbers of ethylene group), trimethylolpropane diacrylate, trimethylolpropane dimethacrylate, trimethylolpropane triacrylate, trimethylolpropane trimethacrylate, trimethylolpropane ethoxytriacrylate, trimethylolpropane ethoxytrimethacrylate, trimethylolpropane propoxytriacrylate, trimethylolpropane propoxytrimethacrylate, tetramethylolmethane triacrylate, tetramethylolmethane trimethacrylate, tetramethylolmethane tetraacrylate, tetramethylolmethane tetramethacrylate, polypropyleneglycol diacrylate (the one having 2 to 14 numbers of propylene group), polypropylene glycol dimethacrylate (the one having 2 to 14 numbers of propylene group), dipentaerythritol pentaacrylate, dipentaerythritol pentamethacrylate, dipentaerythritol hexaacrylate, dipentaerythritol hexamethacrylate, ethoxylated pentaerythritol tetraacrylate (the one having 40 or less numbers of ethoxy group), propoxylated pentaerythritol tetraacrylate (the one having 40 or less numbers of propoxy group), ethoxylated trimethylolpropane triacrylate (the one having 40 or less numbers of ethoxy group), propoxylated trimethylolpropane triacrylate (the one having 40 or less numbers of propoxy groups), bisphenol A polyoxyethylene diacrylate, bisphenol A polyoxyethylene dimethacrylate, bisphenol A dioxyethylene diacrylate, bisphenol A dioxyethylene dimethacrylate, bisphenol A trioxyethylene diacrylate, bisphenol A trioxyethylene dimethacrylate, bisphenol A decaoxyethylene diacrylate, bisphenol A decaoxyethylene dimethacrylate, isocyanuric acid ethoxy modified triacrylate, esterified product with polyvalent carboxylic acid (phthalic anhydride etc.) and the compound having a hydroxy group and an ethylenically unsaturated group (β-hydroxyethyl acrylate, β-hydroxyethyl methacrylate, etc,), alkyl ester (acrylic acid methyl ester, methacrylic acid methyl ester, acrylic acid ethyl ester, methacrylic acid ethyl ester, acrylic acid butyl ester, methacrylic acid butyl ester, acrylic acid 2-ethylhexyl ester, methacrylic acid 2-ethylhexyl ester, etc,) of acrylic acid or methacrylic acid, 2-hydroxyethyl acrylate, 2-hydroxyethyl methacrylate, phenoxyethyl acrylate, phenoxyethyl methacrylate, N,N-dimethylacrylamide, N,N-dimethylaminoethyl acrylate, quaternary chloride by methyl chloride of N,N-dimethylaminoethyl acrylate, quaternary chloride by methyl chloride of N,N-dimethylaminopropylacrylamide, acryloylmorpholine, N-isopropylacrylamide, N,N-diethylacrylamide, etc., among them, dipentaerythritol pentaacrylate, dipentaerythritol pentamethacrylate, dipentaerythritol hexaacrylate, dipentaerythritol hexamethacrylate are preferable, dipentaerythritol pentaacrylate, dipentaerythritol hexaacrylate are more preferable.

Content of the above-described radical polymerizable monomer or oligomer is usually 20% by weight to 60% by weight, preferably 30% by weight to 60% by weight, more preferably 40% by weight to 60% by weight to the weight of the colored composition. Particularly, when used with the compound of the present invention, higher heat resistance effect can be accomplished by using the radical polymerizable monomer or oligomer in 40% by weight to 60% by weight.

The above-described pigment may be the pigment that is used to prepare colored pattern of blue color or green color, for example, pigment of phthalocyanine type, etc. is included. Said phthalocyanine type pigment includes the one including magnesium, titanium, iron, cobalt, nickel, copper, zinc, aluminum in center metal of the molecule, specifically, includes. C.I. pigment blue 15, C.I. pigment blue 15:1, C.I. pigment blue 15:2, C.I. pigment blue 15:3, C.I. pigment blue 15:4, C.I. pigment blue 15:5, C.I. pigment blue 15:6, C.I. pigment blue 16, C.I. pigment blue 17:1, C.I. pigment blue 75, C.I. pigment blue 79, C.I. pigment green 7, C.I. pigment green 36, C.I. pigment green 37. C.I. pigment green 58, chloroaluminum phthalocyanine, hydroxyaluminum phthalocyanine, aluminum phthalocyanine oxide, zinc phthalocyanine, and C.I. pigment blue 15, C.I. pigment blue 15:6, pigment blue 15:1, C.I. pigment blue 15:2, C.I. pigment green 58 are preferable, particularly, C.I. pigment blue 15:6, C.I. pigment green 58 are preferable.

Content of the above-described pigment is 10 to 50% by weight, preferably 10 to 30% by weight to the colored composition.

When the colored composition of the preset invention includes the above-described pigment, it is preferable to contain a pigment dispersant. Said pigment dispersant includes, for example, polyamide amine and salt thereof, polycarboxylic acid and salt thereof, high molecular weight unsaturated acid ester, modified polyurethane, modified polyester, modified poly(meth)acrylate, (meth)acrylic copolymer, naphthalene sulfonic acid formalin condensate, and polyoxyethylene alkyl phosphoric acid ester, polyoxyethylene alkylamine, alkanol amine, etc. Pigment dispersant may be used alone, or in combination of 2 or more kinds. Content thereof is usually 1 to 80% by weight, preferably 10 to 60% by weight to the weight of the pigment.

The above-described solvent may be appropriately selected according to the component included in the colored composition. Specifically, it includes, for example, ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutanoate, ethyl 2-oxobutanoate, diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, methyl ethyl ketone, cyclohexanone, 2-heptanone, 3-heptanone, etc. Content of the solvent is an amount that concentration of the colored composition of the present invention becomes 10% by weight to 80% by weight in solvent.

The above-described silane coupling agent is used in case of binding substrate, such as glass. As said silane coupling agent, the conventionally known one usually used in this field can be used, as reactive organic functional group, for example, silane coupling agent having an epoxy group, a thiol group, a hydroxy group, an amino group, an ureido group, a vinyl group, an acryloyl group, etc is included. Specifically, β-(3,4-epoxycyclohexyl)ethyltrimethoxysilane, γ-glycidooxypropyltrimethoxysilane, γ-mercaptopropyltrimethoxysilane, γ-aminopropyltriethoxysilane, N-β-(aminoethyl)-γ-aminopropyltrimethoxysilane, γ-ureidopropyltriethoxysilane, vinyltriethoxysilane, vinyltri(β-methoxyethoxy)silane, γ-methacryloxypropyltrimethoxysilane are included. The above-described silane coupling agent may be usually used by amount of 0.1% by weight to 10% by weight, preferably by amount of 1% by weight to 5% by weight in the reaction solution.

The above-described cross-linking agent includes (a) epoxy resin, (b) melamine compound, guanamine compound, glycoluril compound or urea compound substituted with at least one substituent selected from a a methylol group, an alkoxymethyl group, and an acyloxymethyl group, (c) phenol compound, naphthol compound or hydroxyanthracene compound substituted with at least one substituent selected from a methylol group, an alkoxymethyl group, and an acyloxymethyl group, among them, polyfunctional epoxy resin is preferable.

This is not particularly limited as long as this is the one which can carry out film curing by cross-linking reaction, and includes, for example, (a) epoxy resin, (b) melamine compound, guanamine compound, glycoluril compound or urea compound substituted with at least one substituent selected from a methylol group, an alkoxymethyl group, and an acyloxymethyl group, (c) phenol compound, naphthol compound or hydroxyanthracene compound substituted with at least one substituent selected from a methylol group, an alkoxymethyl group, and an acyloxymethyl group, among them, polyfunctional epoxy resin is preferable.

Content of the above-described cross-linking agent is 10% by weight to 50% by weight, preferably 20% by weight to 50% by weight to the weight of colored composition.

The colored composition may contain polymerization inhibitor, surfactant, additive, etc. in addition to the above-described one, it is not particularly limited as long as it is the one known per se, and used amount is not limited as long as it is usually amount used in this field.

The colored composition of the present invention is prepared by mixing with the above-described components.

The present invention is further described in detail by example below, but the present invention is not limited to these examples.

EXAMPLE

Synthetic Example 1

Synthesis of Dye Monomer M-1

To 2 L round-bottom flask equipped with stirrer, 47.9 g of rhodamine B (0.10 mol, produced by Wako Pure Chem. Ind., Ltd.), 500 ml of dichloromethane, 15.6 g of hydroxyethyl methacrylate (0.12 mol, produced by Wako Pure Chem. Ind., Ltd.). 4.9 g of 4-dimethylaminopyridine (0.04 mol, produced by Wako Pure Chem. Ind., Ltd.), 32.6 g of I-ethyl-3-(3-dimethylaminopropyl)carbodiimide hydrochloride (0.17 mol, produced by TOYOBO Co., Ltd.) were added, and reacted by stirring at room temperature for 24 hours. After completion of reaction, organic layer was washed with about 500 ml of ion-exchanged water. Then, 50 g of sodium sulfate was added to dehydrate, and 10 mg of p-methoxyphenol (produced by Wako Pure Chem. Ind., Ltd.) was added as polymerization inhibitor, distilled under reduced pressure to remove solvent, to obtain 44 g of red solid (yield: 74.6%). This is referred to dye monomer M-1.

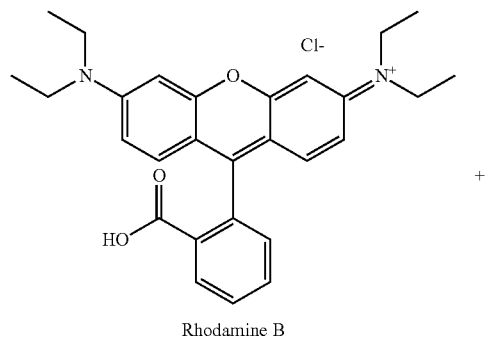

Rhodamine B

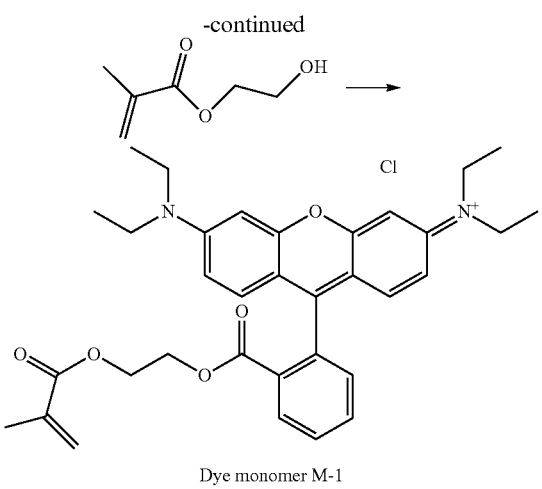

Dye monomer M-1

Example 1

Synthesis of Dye Monomer M-2

To 500 ml round-bottom flask equipped with stirrer, 11.8 g of dye monomer M-1 (0.020 mol), 13.7 g of lithium tetrakis(pentafluorophenyl)borate (0.020 mol, produced by Tosoh-Finechem. Corporation), 150 ml of dichloromethane, 150 ml of ion-exchanged water were added, then, salt-exchanging reaction was carried out by stirring at room temperature for 30 minutes. After completion of reaction, organic layer was washed with 150 ml of ion-exchanged water 4 times. Then, 5 mg of p-methoxyphenol (produced by Wako Pure Chem. Ind., Ltd.) was added to concentrate under reduced pressure, to obtain 22.8 g of red solid (yield, 92.3%) in which a chloride ion of dye monomer M-1 was exchanged to tetrakis(pentafluorophenyl)borate anion. This is referred to dye monomer M-2.

Example 2

Synthesis of Dye Monomer M-3

By the same method as Synthetic Example 2 except for using 4.0 g of 4-nitrobenzene sulfonic acid (0.020 mol, produced by Tokyo Chem. Ind. Ltd.) instead of 13.7 g of lithium tetrakis(pentafluorophenyl)borate, this was synthesized. As a result, 14.4 g of red viscous liquid (yield, 94.7%) in which a chloride ion of dye monomer M-1 was exchanged to 4-nitrobenzenesulfonate anion was obtained. This is referred to dye monomer M-3.

Example 3

Synthesis of Dye Monomer M-4

By the same method as Synthetic Example 2 except for using 5.4 g of sodium pentafluorobenzenesulfonate (0.020 mol, produced by Wako Pure Chem. Ind., Ltd.) instead of 13.7 g of lithium tetrakis(pentafluorophenyl)borate, this was synthesized. As a result, 15.0 g of red viscous liquid (yield, 93.5%) in which a chloride ion of dye monomer M-1 was exchanged to pentafluorobenzenesulfonate anion was obtained. This is referred to dye monomer M-4.

Example 4

Synthesis of Dye Monomer M-5

By the same method as Synthetic Example 2 except for using 3.5 g of 4-fluorobenzenesulfonic acid (0.020 mol, produced by Sigma-Aldrich Corporation) instead of 13.7 g of lithium tetrakis(pentafluorophenyl)borate, this was synthesized. As a result, 13.6 g of red viscous liquid (yield, 93.0%) in which a chloride ion of dye monomer M-1 was exchanged to 4-fluorobenzenesulfonate anion was obtained. This is referred to dye monomer M-5.

Synthetic Example 2

Synthesis of Dye Monomer M-6

By the same method as Synthetic Example 2 except for using 6.6 g of dodecylbenzenesulfonic acid (0.020 mol) instead of 13.7 g of lithium tetrakis(pentafluorophenyl) borate, this was synthesized. As a result, 17.0 g of red viscous liquid (yield, 93.4%) in which a chloride ion of dye monomer M-1 was exchanged to dodecylbenzenesulfonate anion was obtained. This is referred to dye monomer M-6.

Synthetic Example 3

Synthesis of Dye Monomer M-7

By the same method as Synthetic Example 2 except for using 3.8 g of p-toluenesulfonic acid mono-hydrate (0.020 mol) instead of 13.7 g of lithium tetrakis(pentafluorophenyl) borate, this was synthesized. As a result, 13.6 g of red viscous liquid (yield, 91.0/o) in which a chloride ion of dye monomer M-1 was exchanged to p-toluenesulfononate anion was obtained. This is referred to dye monomer M-7.

Synthetic Example 4

Synthesis of Dye Monomer M-8

(1) Hydrolysis of Rhodamine 6G

To the round-bottom flask equipped with stirrer, 12.0 g of rhodamine 6G (compound 1) (0.025 mol, produced by Wako Pure Chem. Ind., Ltd.), 1.1 g of sodium hydroxide (0.026 mol, produced by Wako Pure Chem. Ind., Ltd.), and 80 mL of ethanol (produced by Wako Pure Chem. Ind., Ltd.) were added, and reacted for 12 hours at 70° C. After distilling off the solvent under vacuum concentration, 130 mL of ion exchanged water was added, 1 mol/L of HCL aqueous solution was added dropwise until pH reaches about 2, and stirred for 1 hour. By filtering the deposited crystal, 10.3 g (yield, 91%) of hydrolysate of rhodamine 6G (compound 2) was obtained.

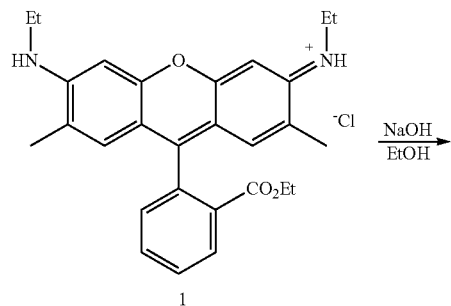

1

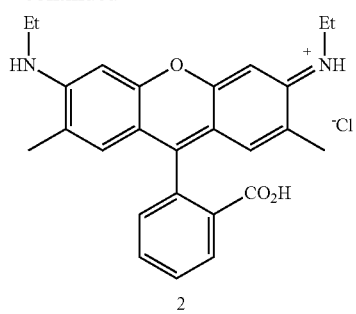

2

(2) Synthesis of Dye Monomer M-8

To the round-bottom flask equipped with stirrer, 10.2 g of hydrolysate of rhodamine 6G (compound 2) (0.023 mol), 3.5 g of 2-hydroxyethyl methacrylate (compound 3) (0.027 mol, produced by Wako Pure Chem. Ind., Ltd.), 0.8 g of 4-dimethylaminopyridine (0.007 mol, produced by Wako Pure Chem. Ind., Ltd.), 7.4 g of 1-ethyl-3-(3-dimethylaminopropyl)carbodiimide hydrochloride (0.038 mol, produced by TOYOBO Co., Ltd.), 90 mL of dichloromethane (produced by Wako Pure Chem. Ind., Ltd.) were added, and reacted at room temperature for 24 hours. After completion of reaction, this was washed by adding ion-exchanged water, distilled off the solvent under vacuum concentration. Further, this was purified by silica-gel column chromatography, distilled off the solvent under vacuum concentration, 12.1 g of brown solid of dye monomer M-8 (compound 4) (yield, 95%) was obtained.

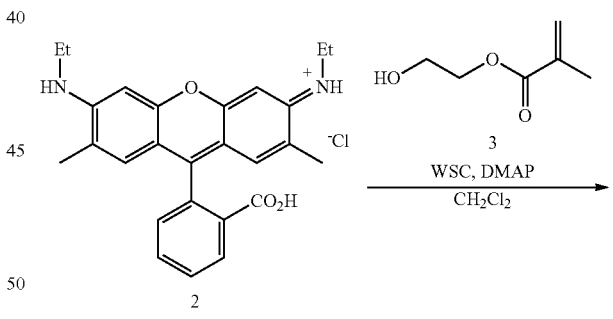

2

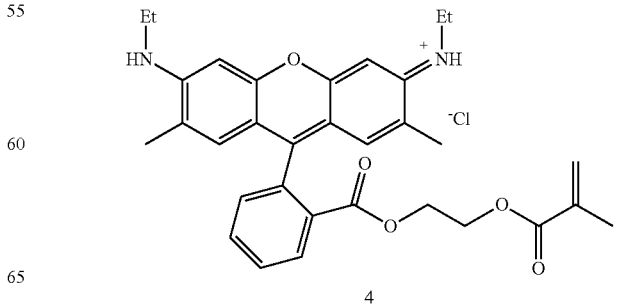

4

Example 5

Synthesis of Dye Monomer M-9

To the round-bottom flask equipped with stirrer, 9.0 g of dye monomer M-8 (compound 4) (0.016 mol), 10.9 g of lithium tetrakis(pentafluorophenyl)borate (0.016 mol, produced by Tosoh-Finechem. Corp.), 110 ml of dichloromethane (produced by Wako Pure Chem. Ind., Ltd.), and 30 ml of ion-exchanged water were added, then, reacted at room temperature for 3 hours, salt-exchange reaction was carried out. After completion of reaction, aqueous layer was separated, washed with ion-exchanged water. Then, aqueous layer was concentrated under reduced pressure, 19.3 g of brown solid (compound 5) (yield, 100%) in which a chloride ion of dye monomer M-8 was exchanged to tetrakis(pentafluorophenyl)borate anion was obtained. This is referred to dye monomer M-9.

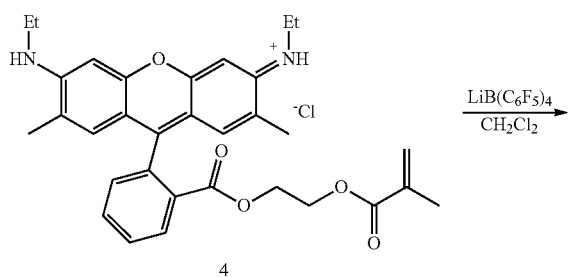

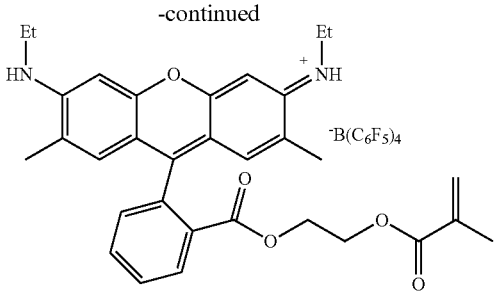

Synthetic Example 5

Synthesis of Dye Monomer M-10

To the round-bottom 2 L flask equipped with stirrer, 47.9 g of rhodamine B (0.10 mol, produced by Wako Pure Chem. Ind., Ltd.), 500 ml of dichloromethane, 17.3 g of hydroxybutyl acrylate (0.12 mol, produced by Wako Pure Chem. Ind., Ltd.), 4.9 g of 4-dimethylaminopyridine (0.04 mol, produced by Wako Pure Chem. Ind., Ltd.), 32.6 g of 1-ethyl-3-(3-dimethylaminopropyl)carbodiimide hydrochloride (0.17 mol, produced by TOYOBO Co., Ltd.) were added, and reacted by stirring at room temperature for 24 hours. After completion of reaction, organic layer was washed with about 500 ml of ion-exchanged water. Then, 50 g of sodium sulfate was added to dehydrate, 10 mg of p-methoxyphenol as polymerization inhibitor (produced by Wako Pure Chem. Ind., Ltd.) was added, and distilled off the solvent under reduced pressure to obtain 48.5 g of red solid (yield, 80.2%). This is referred to dye monomer M-10.

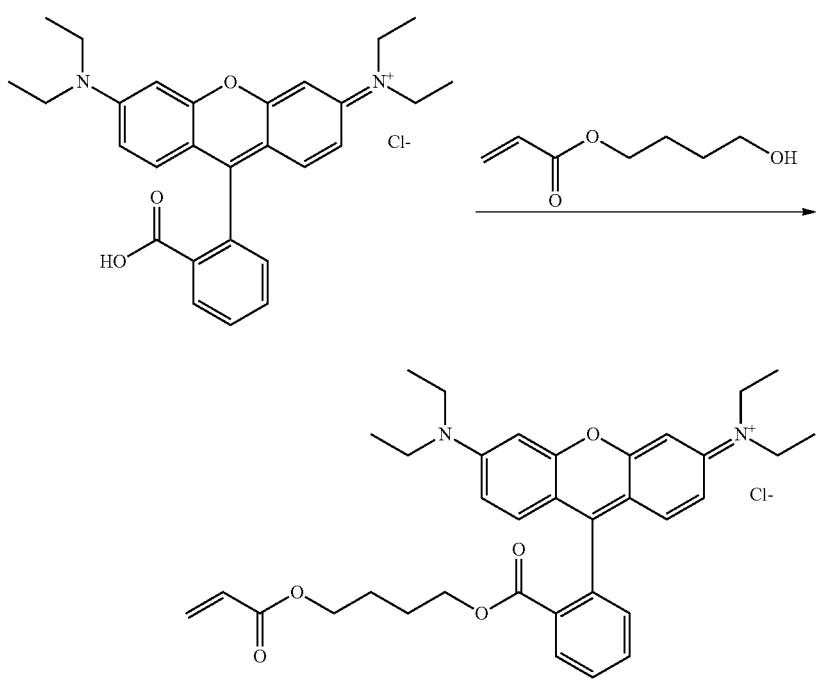

Example 6

Synthesis o Dye Monomer M-11

To 500 ml round-bottom flask equipped with stirrer, 12.1 g of dye monomer M-10 (0.020 mol), 13.7 g of lithium tetrakis(pentafluorophenyl)borate (0.020 mol, produced by Tosoh-Finechem. Corp.), 150 ml of dichloromethane, 150 ml of ion-exchanged water were added, then, salt exchanging reaction was carried out by stirring at room temperature for 30 minutes. After completion of reaction, organic layer was washed with about 150 ml of ion-exchanged water 4 times. Then, 5 mg of p-methoxyphenol (produced by Wako Pure Chem. Ind., Ltd.) was added, concentrated under reduced pressure, and 23.5 g of red solid (yield, 93.9%) in which a chloride ion of dye monomer M-10 was exchanged to tetrakis(pentafluorophenyl)borate anion was obtained. This is referred to dye monomer M-11.

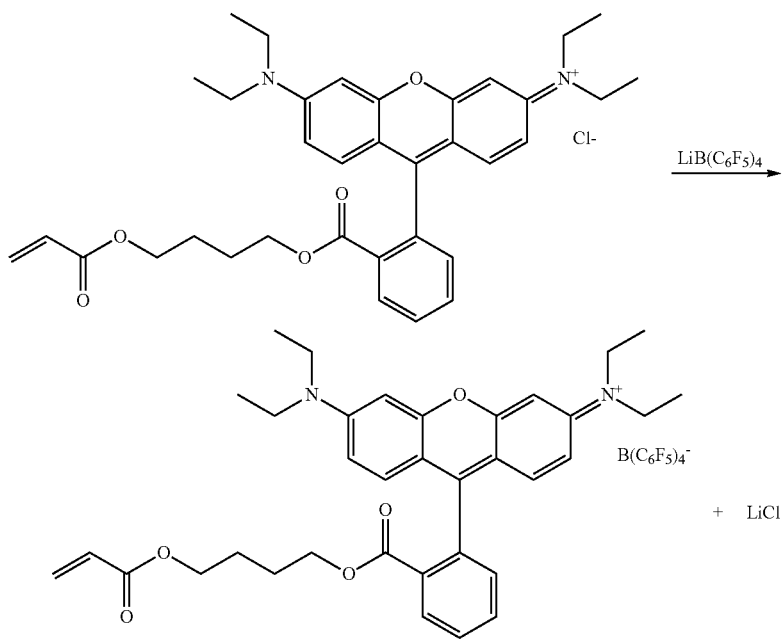

Synthetic Example 6

Synthesis of Dye Monomer M-12 ($B(C_6F_5)_4$ salt of Rhodamine B)

To 500 ml round-bottom flask equipped with stirrer, 9.6 g of rhodamine B (0.020 mol), 13.7 g of lithium tetrakis (pentafluorophenyl)borate (0.020 mol, produced by Tosoh-Finechem. Corp.), 150 ml of dichloromethane, 150 ml of ion-exchanged water were added, then, salt exchanging reaction was carried out by stirring at room temperature for 30 minutes. After completion of reaction, organic layer was washed with about 150 ml of ion-exchanged water 4 times. Then, concentrated under reduced pressure, 21.1 g of red solid (yield, 94.0%) in which a chloride ion of rhodamine B was exchanged to tetrakis(pentafluorophenyl)borate anion was obtained. This is referred to dye monomer M-12.

Example 7

Synthesis Of Dye Polymer P-2

To 200 ml round-bottom flask equipped with stirrer, condenser, thermometer, nitrogen introducing pipe, 27.9 g of propylene glycol monomethyl ether acetate (produced by Wako Pure Chem. Ind., Ltd.) was added, and heated under nitrogen gas stream until inner temperature reaches 90° C. Then, solution mixed with 3.0 g of dye monomer M-2, 50.1 g of benzyl methacrylate (produced by Wako Pure Chem. Ind., Ltd.), 6.9 g of methacrylic acid (produced by Wako Pure Chem. Ind., Ltd.), 9.6 g of dimethyl 2,2'-azobis(2-methylpropionate) (produced by Wako Pure Chem. Ind., Ltd, Polymerization inhibitor V-601), and 27.9 g of propylene glycol monomethyl ether acetate (produced by Wako Pure Chem. Ind., Ltd.) was added dropwise into the round-bottom flask over 2 hours. Then, the obtained solution was reacted at 90° C. for 2 hours. After completion of reaction, this was cooled until room temperature, 48.6 g of propylene glycol monomethyl ether acetate was added to dilute, thus, dye polymer was obtained. This is referred to dye polymer P-2 (weight ratio: dye monomer M-2/benzyl methacrylate/methacrylic acid=3.0/50.1/6.9).

Example 8 to 10

Synthesis of Dye Polymer P-3 to 5

By the same method as Synthetic Example 1 except for using dye monomer M-3 instead of dye monomer M-2, dye polymer was obtained. This is referred to dye polymer P-3. Also, similarly, dye polymer P-4 and P-5 were obtained by using dye monomer M-4 or 5 instead of dye monomer M-2.

Synthetic Example 7 to 9

Synthesis of Dye Polymer P-1, 6 and 7

By the same method as Synthetic Example 1 except for using dye monomer M-1, 6 or 7 instead of dye monomer M-2, dye polymer was obtained. These are referred to dye polymer P-1, P-6, P-7, respectively.

Example 11

Synthesis of Dye Polymer P-8 (Synthesis of Polymer Having High Ratio of Dye Monomer)

To 200 ml round-bottom flask equipped with stirrer, condenser, thermometer, nitrogen introducing pipe, 11.6 g of propylene glycol monomethyl ether acetate (produced by Wako Pure Chem. Ind., Ltd.) was added, heated under nitrogen gas stream until inner temperature reaches 90° C. Then, solution mixed with 20 g of dye monomer M-2, 2.1 g of benzyl methacrylate (produced by Wako Pure Chem. Ind., Ltd.), 2.9 g of methacrylic acid (produced by Wako Pure Chem. Ind., Ltd.), 4 g of dimethyl 2,2'-azobis(2-methyl propionate) (produced by Wako Pure Chem. Ind., Ltd; polymerization inhibitor V-601), and 11.6 g of propylene glycol monomethyl ether acetate (produced by Wako Pure Chem. Ind., Ltd.) were added dropwise into the round-bottom flask over 2 hours. Then, the obtained solution was reacted at 90° C. for 2 hours. After completion of reaction, this was cooled until room temperature, 20.2 g of propylene glycol monomethyl ether acetate was added to dilute, thus, dye polymer was obtained. This is referred to dye polymer P-8 (weight ratio: dye monomer M-2/benzyl methacrylate/methacrylic acid=80/8.5/11.5).

Example 12

Synthesis of Dye Polymer P-9

By the same method as Synthetic Example 1 except for using dye monomer M-9 instead of dye monomer M-2, dye polymer was obtained. This is referred to dye polymer P-9.

Example 13

Synthesis of Dye Polymer P-11

By the same method as Synthetic Example 1 except for using dye monomer M-1 instead of dye monomer M-2, dye polymer was obtained.
This is referred to dye polymer P-11.

Example 14

Synthesis of Dye Polymer P-12 (Synthesis of Polymer Having High Ratio of Dye Monomer)

To 100 ml round-bottom flask equipped with stirrer, condenser, thermometer, nitrogen introducing pipe, 9.3 g of propylene glycol monomethyl ether acetate (produced by Wako Pure Chem. Ind., Ltd.) was added, and heated under nitrogen gas stream until inner temperature reaches 90° C. Then, solution mixed with 16 g of dye monomer M-2, 4 g of benzyl methacrylate (produced by Wako Pure Chem. Ind., Ltd.), 3.2 g of dimethyl 2,2'-azobis(2-methylpropionate) (produced by Wako Pure Chem. Ind., Ltd; polymerization inhibitor V-601), and 9.3 g of propylene glycol monomethyl ether acetate (produced by Wako Pure Chem. Ind., Ltd.) were added dropwise into the round-bottom flask over 2 hours. Then, the obtained solution was reacted at 90° C. for 2 hours. After completion of reaction, this was cooled until room temperature, 16.2 g of propylene glycol monomethyl ether acetate was added to dilute, thus, dye polymer was obtained. This is referred to dye polymer P-12 (weight ratio: dye monomer M-2/benzyl methacrylate=80/20). Concentration of non-volatile component of this polymer was 35.7%.

Example 15

Synthesis of Dye Polymer P-13 (Synthesis of Polymer having High Ratio of Dye Monomer)

By the same method as Synthetic Example 10 except for using dye monomer M-11 instead of dye monomer M-2, dye polymer was obtained. This is referred to dye polymer P-12 (weight ratio: dye monomer M-11; benzyl methacrylate=80/20). Concentration of non-volatile component was 34.3%.

Example 16

Synthesis Of Dye Polymer P-14

Except for changing 50.1 g of benzyl methacrylate to 32.1 g of benzyl methacrylate and 18 g of mono(2-methacryloyloxyethyl) succinate (produced by Shin-Nakamura Chemical Co., Ltd, NK ester SA), dye polymer was obtained by the same method as Example 7. This is referred to dye polymer P-14 (weight ratio: dye monomer M-2/benzyl methacrylate/mono(2-methacryloyloxyethyl)succinate/methacrylic acid=5/53.5/30/11.5).

Example 17

Synthesis of Dye Polymer P-15

By the same method as Synthetic Example 7 except for changing 50.1 g of benzyl methacrylate to 32.1 g of methyl methacrylate and 18 g of mono (2-methacryloyloxyethyl) succinate, dye polymer was obtained. This is referred to dye polymer P-15 (weight ratio: dye monomer M-2/methyl methacrylate/mono(2-methacryloyloxyethyl)succinate/methacrylic acid=5/53.5/30/11.5).

Example 18

Synthesis of Dye Polymer P-16

By the same method as Synthetic Example 7 except for changing 50.1 g of benzyl methacrylate to 32.1 g of methyl methacrylate and 18 g of diethylacrylamide (produced by Wako Pure Chem. Ind., Ltd.), dye polymer was obtained. This is referred to dye polymer P-16 (weight ratio: dye monomer M-2/methyl methacrylate/diethylacrylamide/methacrylic acid=5/53.5/30/11.5).

Example 19

Synthesis of Dye Polymer P-17

By the same method as Synthetic Example 7 except for changing 50.1 g of benzyl methacrylate to 32.1 g of methyl methacrylate and 18 g of styrene (produced by Wako Pure Chem. Ind., Ltd.), dye polymer was obtained. This is referred to dye polymer P-17 (weight ratio: dye monomer M-2/methyl methacrylate/styrene/methacrylic acid=5/53.5/30/11.5).

Example 20

Synthesis of Dye Polymer P-18

By the same method as Synthetic Example 7 except for changing 50.1 g of benzyl methacrylate with 32.1 g of methyl methacrylate, 18 g of N-phenylmaleimide, dye polymer was obtained. This is referred to dye polymer P-18 (weight ratio: dye monomer M-2/methyl methacrylate/N-phenylmaleimide/methacrylic acid=5/53.5/30/11.5).

Example 21

Heat Resistance Evaluation of Polymer (230° C. 0.5 hours)

Heat resistance of dye polymer P-2 to P-5, P-9 and P-11 obtained in Example 5 to 8 was evaluated as described below.

That is, after the obtained dye polymer P-2 to P-5, P-9 and P-11 was spin coated onto 3 inch glass-wafer (manufactured by Corning Inc., Eagle XG), respectively, and thin film having film thickness of 1μ was obtained by drying for 90 second on the hot plate heated at 90° C. Absorbance (λa) in maximum absorption wavelength of these obtained thin films were measured, respectively, by using spectrophotometer (manufactured by Shimadzu Corp., Spectrophotometer UV-2550), then, after heating for 30 minutes on the hot plate heated at 230° C., absorbance (λb) thereof was measured again. From the value of λa and λb, dye residual ratio (%) was determined by the following formula. In addition, the obtained dye residual ratio was evaluated according to to the following criteria.

Dye Residual Ratio (%)=(λb/λa)×100

[Criteria]
⊚: dye residual ratio ≥81%;
○: 61%≤dye residual ratio<80%;
Δ: 51%≤dye residual ratio<60%;
x: dye residual ratio≤50%;
The obtained results are shown in Table-1.

Comparative Example 1

Heat Resistance Evaluation of Polymer (230° C. 0.5 Hours)

By the same method as Synthetic Example 21 except for using dye polymer P-1, 6 or 7 instead of dye polymer P-2 to P-5, P-9 and P-11, heat resistance evaluation of dye polymer P-1, 6 and 7 was carried out. The obtained results are shown in Table-1.

Example 22

Heat Resistance Evaluation of Monomer (230° C., 0.5 Hours)

Heat resistance of dye monomer M-2 to M-5, M-9 and M-11 obtained in Example 1 to 6 was evaluated as below.
(1) Synthesis of Polymer not Including Dye To 500 ml round-bottom flask equipped with stirrer, condenser, thermometer, nitrogen introducing pipe, 98.5 g of propylene glycol monomethyl ether acetate (produced by Wako Pure Chem. Ind., Ltd.) was added, and heated under nitrogen gas stream until inner temperature reaches 90° C. Then, solution mixed with 186.2 g of benzyl methacrylate, 25.6 g of methacrylic acid, 33.9 g of dimethyl 2,2'-azobis (2-methylpropionate) (produced by Wako Pure Chem. Ind., Ltd; polymerization inhibitor V-601), and 98.5 g of propylene glycol monomethyl ether acetate were added dropwise into the round-bottom flask over 2 hours. Then, the obtained solution was reacted at 90° C. for 2 hours. After completion of reaction, this was cooled until room temperature, 171.5 g of propylene glycol monomethyl ether acetate was added to dilute, thus, the pale yellow transparent polymer solution was obtained. This is referred to dye polymer A. In addition, concentration of non-volatile component was 35.9%.
(2) Preparation of Dye Monomer Mixing Solution 1 g of dye monomer (M-2 to M-4, M-9 or M-11), 52.9 g of Polymer A, and 3.2 g of propylene glycol monomethyl ether acetate were mixed to prepare dye monomer mixing solution B.
(3) Heat Resistance Evaluation By the same method as Synthetic Example 21 except for using dye monomer mixing solution B instead of dye polymer P-2 to P-5, heat resistance was evaluated.

Comparative Example 2

Heat Resistance Evaluation of Monomer (230° C. 0.5 Hours)

By the same method as Synthetic Example 21 except for using dye monomer M-1, 6 or 7 instead of dye monomer M-2 to M-5, M-9 and M-11, each of heat resistance evaluation of dye polymer P-1, 6 and 7 was carried out. The obtained results are shown in Table 1 in conjunction with Example 21, Example 22, and Comparative Example 1.

TABLE 1

|  | Dye Polymer | Dye Residual Ratio (%) | Heat Resistance Evaluation |  | Dye monomer | Dye Residual Ratio (%) | Heat Resistance Evaluation |
|---|---|---|---|---|---|---|---|
| Example 21 | P-2 | 90 | ⊚ | Example 22 | M-2 | 83 | ⊚ |
|  | P-3 | 87 | ⊚ |  | M-3 | 84 | ⊚ |
|  | P-4 | 85 | ⊚ |  | M-4 | 82 | ⊚ |
|  | P-5 | 80 | ○ |  | M-5 | — | — |
|  | P-9 | 92 | ⊚ |  | M-9 | 90 | ⊚ |
|  | P-11 | 89 | ⊚ |  | M-11 | 82 | ⊚ |
| Comparative Example 1 | P-6 | 76 | ○ | Comparative Example 2 | M-6 | 66 | X |
|  | P-7 | 72 | ○ |  | M-7 | 58 | X |
|  | P-1 | 12 | X |  | M-1 | 5 | X |

As shown in the above-described Table-1, it is found that dye polymer P-2 to P-5, P-9 and P-11 of Example 21 as well as dye monomer M-2 to M-4, M-9 and M-11 of Example 22 show higher heat resistance than that of dye monomer M-1, M-6 and M-7, dye polymer P-1, P-6, P-7 in Comparative Example 1 and 2.

In Comparative Example 2 and Example 22, anion components in dye monomer M-1, M-6 and M-7 are different from dye monomer M-2 to M-4, M-9 and M-11, therefore, it was considered that heat resistance is improved by using tetrakis(pentafluorophenyl)borate anion, 4-nitrobenzenesulfonate anion, pentafluorobenzenesulfonate anion as anion component. In addition, P-5 of Example 21 showed also excellent effect of heat resistance, therefore, it was considered that heat resistance is similarly improved even by using 4-fluorobenzenesulfonate anion as anion component.

In addition, dye residual ratio of dye polymer of Example 21 is higher than that of dye monomer of Example 22, therefore, it was found that heat resistance is further improved by polymerization of a monomer.

Example 23

Heat Resistance Evaluation of Polymer (230° C. 1.5 Hours)

By the same method as Synthetic Example 21 except for changing the heating time from 30 minutes to 90 minutes, and using dye polymer P-2 to P-4, P-9, P-10, P-11, P-13 to P-17, heat resistance evaluation of these polymers was carried out. The obtained results are shown in Table-2.

Comparative Example 3

Heat Resistance Evaluation of Polymer (230° C., 1.5 Hours)

By the same method as Synthetic Example 21 except for using dye polymer P-1, 6 or 7 instead of dye polymer P-2 to P-4, heat resistance evaluation of dye polymer P-1, 6 and 7 was carried out. The obtained results are shown in Table-2.

Example 24

Heat Resistance Evaluation of Monomer (230° C. 1.5 Hours)

By the same method as Synthetic Example 22 except for changing the heating time from 30 minutes to 90 minutes, heat resistance evaluation of dye polymer M-2 to 4, M-9. M-10 and M-11 was carried out.
The obtained results are shown in Table-2.

Comparative Example 4

Heat Resistance Evaluation of Monomer (230° C., 1.5 Hours

By the same method as Synthetic Example 22 except for changing the heating time from 30 minutes to 90 minutes, heat resistance evaluation of dye polymer M-1, M-6 and M-7 was carried out.
The obtained results are shown in Table-2 in conjunction with Example 23, Example 24 and Comparative Example 3.

TABLE 2

|  | Dye Polymer | Dye Residual Ratio (%) | Heat Resistance Evaluation |  | Dye monomer | Dye Residual Ratio (%) | Heat Resistance Evaluation |
| --- | --- | --- | --- | --- | --- | --- | --- |
| Example 23 | P-2 | 77 | ◯ | Example 24 | M-2 | 69 | ◯ |
|  | P-3 | 72 | ◯ |  | M-3 | 57 | Δ |
|  | P-4 | 68 | ◯ |  | M-4 | 55 | Δ |
|  | P-9 | 83 | ⊚ |  | M-9 | 72 | ◯ |
|  | P-11 | 78 | ◯ |  | M-11 | 70 | ◯ |
|  | P-13 | 76 | ◯ |  |  |  |  |
|  | P-14 | 78 | ◯ |  |  |  |  |
|  | P-15 | 76 | ◯ |  |  |  |  |
|  | P-16 | 76 | ◯ |  |  |  |  |
|  | P-17 | 79 | ◯ |  |  |  |  |
| Comparative | P-6 | 43 | X | Comparative | M-6 | 31 | X |
| Example 2 | P-7 | 42 | X | Example 4 | M-7 | 33 | X |
|  | P-1 | 3 | X |  | M-1 | 2 | X |

In Example 23, Example 24, Comparative Example 3 and Comparative Example 4, heat resistance was evaluated by changing the heating time of the above-described Example 21, Example 22, Comparative Example 1 and Comparative Example 2 from 30 minutes to 90 minutes, respectively.

As shown in Table 2, similarly to the case of heating times of 30 minutes, dye polymer P-2 to P-4, P-9 and P-1 of Example 23 as well as dye monomer M-2 to M-4, M-9 and M-11 of Example 24 showed higher heat resistance, respectively, than that of dye polymer P-1, P-6, P-7, and dye monomer M-1, M-6, M-7 having different anion component from them. Particularly, it was found that dye monomer M-2, M-9 and M-11 using tetrakis(pentafluorophenyl)borate anion as anion as well as dye polymer P-2, P-9, P-11, and P-13 to 17 containing these monomers showed high heat resistance. In addition, it was found that dye polymer has more excellent heat resistance comparing with that of dye monomer.

On the other hand, dye residual ratio of P-1, P-6 and P-7 of Comparative Example 3, and, M-1, M-6 and M-7 of Comparative Example 4 significantly decreased comparing to the case of 30 minutes heating (Comparative Example 1 and 2). In case of using dye polymer and dye monomer of Example 23 and 24, although dye residual ratio was decreased, further large difference was observed in decreasing ratio.

Example 25

Solvent Resistance Evaluation of Cured Film of Dye Polymer P-12

By using dye polymer P-12 obtained by Example 14, and preparing simple ultraviolet curable color resist, solvent resistance of cured film for propylene glycol monomethyl ether acetate was evaluated.

That is, resist solution was obtained by mixing dye polymer P-12/polymer A/dipentaerythritol hexaacrylate/2-benzyl-2-dimethylamino-1-(4-morpholinophenyl)-butanone-1/3-methacryloxypropyltrimethoxysilane, so that their ratio is 18.8/36.2/30/10/5 in weight ratio of non-volatile component. This resist solution was spin coated onto 3 inches glass wafer, respectively, then, thin film having 1.5μ film thickness was obtained by drying for 100 seconds on the hot-plate heated at 100° C. After each of the obtained thin film was irradiated with light intensity of 200 mJ/cm² by using a high-pressure mercury lamp, and immersed in 0.5% KOH aqueous solution for 90 seconds, it was washed with ion-exchanged water, further, heated on the hot-plate heated at 230° C. for 30 minutes.

Absorbance (λc) in maximum absorption wavelength by using spectrophotometer was measured, then, after immersing in solution of propylene glycol monomethyl ether for 2 hours, and after heating for 100 seconds on the hot-plate heated at 100° C., absorbance (λd) was measured again. From the value of λc and λd, dye residual ratio (%) was determined according to the following formula. The obtained dye residual ratio was used as an index of solvent resistance.

Dye residual ratio (%)=(λd/λc)×100

Resist composition and result of solvent resistance were shown in Table 3.

Example 26

Solvent Resistance Evaluation of Cured Film of Dye Polymer P-13

By the same method as Synthetic Example 25 except for using dye monomer P-13 instead of dye polymer P-12, solvent resistance of dye polymer P-13 was evaluated. The obtained result was shown in Table 3 in conjunction with Example 25.

Example 27

Solvent Resistance Evaluation of Cured Film of Dye Monomer M-2

By the same method as Synthetic Example 25 except for using dye monomer M-2 instead of dye polymer P-12, and mixing dye monomer M-2/polymer A/dipentaerythritol hexaacrylate/2-benzyl-2-dimethylamino-1-(4-morpholinophenyl)-butanone-1/3-methacryloxypropyltrimethoxysilane, so that their ratio is 15/40/30/10/5 in weight ratio of non-volatile component, heat resistance of dye monomer M-2 was evaluated. Resist composition and the result of solvent resistance were shown in Table 3 in conjunction with the result of Example 25, 26.

Example 28

Solvent Resistance Evaluation of Cured Film of Dye Monomer M-11

By the same method as Synthetic Example 27 except for using dye monomer M-11 instead of dye monomer M-2, heat resistance of dye monomer M-11 was evaluated. Resist composition and result of solvent resistance were shown in Table 3 in conjunction with the result of Example 25 to 27.

Comparative Example 5

Solvent Resistance Evaluation of Cured Film of Dye Monomer M-12

By the same method as Synthetic Example 27 except for using dye monomer M-12 instead of dye monomer M-2, heat resistance of dye monomer M-12 was evaluated. Resist composition and the result of solvent resistance were shown in Table 3 in conjunction with the result of Example 25 to 28.

TABLE 3

| | | Example 25 | Example 26 | Example 27 | Example 28 | Comparative Example 5 |
|---|---|---|---|---|---|---|
| Solvent resistance to PGMEA (dye residual ratio: %) | | 90 | 89 | 79 | 78 | 43 |
| Composition of Resist Number in ( ) indicates weight of non-volatile component | Dye polymer | P-12 53 g (18.8 g) | P-13 55 g (18.8 g) | | | |
| | Dye monomer | | | M-2 15 g | M-11 15 g | M-12 15 g |
| | Polymer A | 101 g (36.2 g) | 101 g (36.2 g) | 111 g (40 g) | 111 g (40 g) | 111 g (40 g) |
| | KAYARAD DPHA | 30 g | 30 g | 30 g | 30 g | 30 g |
| | IRGACURE 369 | 10 g | 10 g | 10 g | 10 g | 10 g |
| | LS-3380 | 5 g | 5 g | 5 g | 5 g | 5 g |
| | PGMEA | 87 g | 85 g | 115 g | 115 g | 115 g |

KAYARAD DPHA: dipentaerythritol hexaacrylate (produced by Nippon Kayaku Co., Ltd.);
IRGACURE 369: 2-benzyl-2-dimethylamino-1-(4-moipholinophenyl)-butanone-1 (produced by BASF Ltd.);
LS-3380: 3-methacryloxypropylyrimethoxysilane (produced by Shin-Etsu Chemical Co., Ltd.);
PGMEA: propylene glycol monomethyl ether acetate;
NMP: N-methyl-2-pyrrolidone;

In the color filter, usually, after pattern was formed by the polymer including first color on the substrate, pattern is formed by the polymer including second color. On this occasion, the pattern formed polymer is exposed in the solvent including the second color. On this occasion, dye elution from the pattern formed polymer to solvent causes reduction of color concentration and simultaneously color mixture with the second color. Thus, solvent resistance of cured polymer becomes an important factor.

As is clear from Table 3, in case of using P-12, P-13, M-2 or M-11 as dye, solvent resistance to solvent is very high and dye residual ratio was almost more than 90%. On the other hand, solvent resistance of M-12 used in Comparative Example 5 was as low as 43%. It was considered that this is due to unfixed state in the cured film because anion is a chloride ion, and rhodamine B having non-polymerizable group, Since dye polymers P-12, P-13 used in Example 25, 26 were the polymerized one of dye monomer M-2, M-11 in Example 27, 28, respectively, by the result of Table 3, it was found that the case of adding in the form of dye polymer to resist gives higher solvent resistance than the case of adding to resist in the form of dye monomer.

Example 29 to 31

Solvent Resistance Evaluation of Cured Film Due to Difference in Amount of Cross-Linking Agent (Dye Monomer M-2)

By the same method as Synthetic Example 27 except for using resist solution obtained by mixing dye monomer M-2/polymer A/dipentaerythritol hexaacrylate/2-benzyl-2-dimethylamino-1-(4-morpholinophenyl)-butanone-1/3-methacryloxypropyltrimethoxysilane, so that their ratio is 15/25/45/10/5 (Example 29), 15/10/60/10/5 (Example 30), or 15/0/70/10/5 (Example 31) in weight ratio of non-volatile component solvent resistance was evaluated. Resist composition and the result of evaluation were shown in Table 4.

Example 32 to 34

Solvent Resistance Evaluation of Cured Film Due to Difference in Amount of Cross-linking Agent (Dye Monomer M-11)

By the same method as Synthetic Example 28 except for using resist solution obtained by mixing dye monomer M-11/polymer A/dipentaerythritol hexaacrylate/2-benzyl-2-dimethylamino-1-(4-morpholinophenyl)-butanone-1/3-methacryloxypropyltrimethoxysilane, so that their ratio is 15/25/45/10/5 (Example 32), 15/10/60110/5 (Example 33), or 15/0/70/10/5 (Example 34), in weight ratio of non-volatile component and solvent resistance was evaluated. Resist composition and the result of evaluation are shown in Table 4.

From the results of Example 29, 30, 32, and 33 in which amount of DPHA of radical polymerizable poly-functional monomer increased more than that of Example 27 and 28, it is found that heat resistance was improved comparing with solvent resistance of Example 27 and 28. It was considered that this was because elution to PEGMEA was suppressed due to increasing of the cross-linking density of the cured film. From this result, when cured film was prepared by using the monomer of the present invention, it was found that elution of dye was suppressed by increasing blending ratio of polymerizable poly-functional monomer like DPHA.

In addition, because in Example 31 and 34 in which all of polymer components A changed to DPHA, film was broken after UV irradiation and peeled off from substrate, therefore, measurement of solvent resistance was not able. It was considered that this was due to decreasing of adhesion to the substrate because of occurrence of the strong curing shrinkage of the film after UV-irradiating by removal of polymer component A.

Example 35

Synthesis of Dye Monomer M-21

(1) Synthesis of 4-hydroxybutyl methacrylate 135 g of 1,4-butandiol (1.5 mol, produced by Wako Pure Chem. Ind., Ltd.), 96 g of 1-ethyl-3-(3-dimethylaminopropyl)carbodiimide hydrochloride (0.5 mol, produced by TOYOBO Co., Ltd.), 1.2 g of N,N-dimethylaminopyridine (produced by Wako Pure Chem. Ind., Ltd.) were dissolved into 2 L of dichloromethane. Then, 43 g of methacrylic acid (0.5 mol, produced by Wako Pure Chem. Ind., Ltd.) was added dropwise, stirred at room temperature for 12 hours. Thereafter, solvent was distilled off under reduced pressure by using rotary evaporator, purified by silica gel column chromatography using solution mixed with 1/1 of hexane/ethyl acetate by volume ratio as elution solvent to obtain 50 g of colorless oily 4-hydroxybutyl methacrylate (yield, 63%).

(2) Addition Reaction of Butyl Methacrylate to Rhodamine B

Into 2 L round-bottom flask equipped with stirrer, 47.9 g of rhodamine B (0.10 mol, produced by Wako Pure Chem. Ind., Ltd.), 500 ml of dichloromethane, 19.0 g of 4-hydroxybutyl methacrylate obtained in the above-described (1) (0.12 mol), 4.9 g of 4-dimethylaminopyridine (0.04 mol, produced by Wako Pure Chem. Ind., Ltd.), 32.6 g of 1-ethyl-3-(3-dimethylaminopropyl)carbodiimide hydrochloride (0.17 mol, produced by TOYOBO Co., Ltd.) were added, reacted by stirring at room temperature for 24 hours. After completion of reaction, organic layer was washed with about 500 ml of ion-exchanged water. Then, it was dehydrated by adding 50 g sodium sulfate, and solvent was distilled off under

TABLE 4

| | | Example 29 | Example 30 | Example 31 | Example 32 | Example 33 | Example 34 |
|---|---|---|---|---|---|---|---|
| Solvent Resistance to PGMEA (Dye Residual Rato: %) | | 86 | 89 | Unmeasurable | 87 | 89 | Unmeasurable |
| Resist Composition Number in ( ) shows Weight of No-Volatile Matter | Dye Monomer | M-2 | M-2 | M-2 | M-11 | M-11 | M-11 |
| | | 15 g | 15 g | 15 g | 15 g | 15 g | 15 g |
| | Polymer A | 70 g (25 g) | 28 g (10 g) | | 70 g (25 g) | 28 g (10 g) | |
| | KAYARAD DPHA | 45 g | 60 g | 70 g | 45 g | 60 g | 70 g |
| | IRGACURE 369 | 10 g | 10 g | 10 g | 10 g | 10 g | 10 g |
| | LS-3380 | 5 g | 5 g | 5 g | 5 g | 5 g | 5 g |
| | PGMEA | 141 g | 168 g | 186 g | 141 g | 168 g | 186 g | reduced pressure by adding 10 mg of p-methoxyphenol (produced by Wako Pure Chem. Ind., Ltd.) as polymerization inhibitor, and 52.6 g (yield, 85.0%) of red solid was obtained.

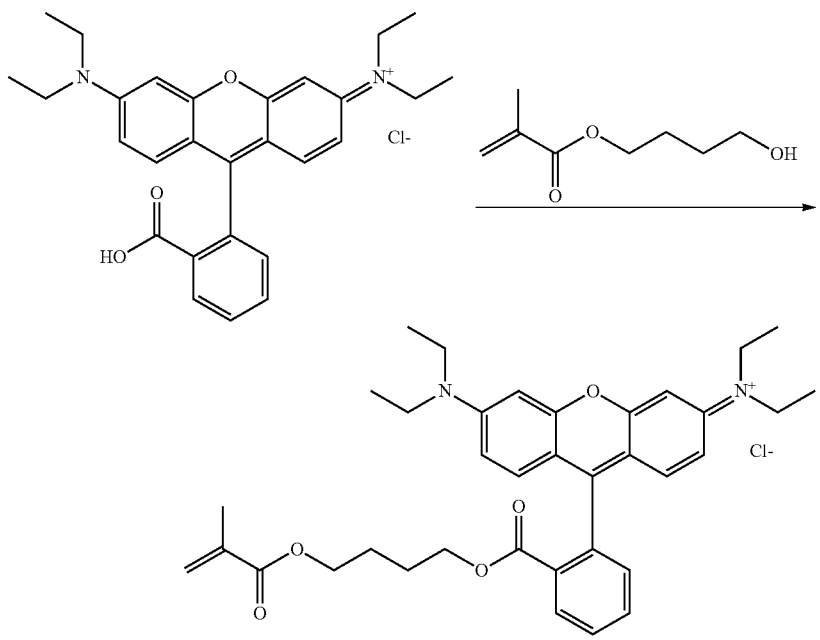

(3) Anion Exchanging Reaction

In 1 L round-bottom flask equipped with stirrer, 37.2 g (0.060 mol) of red solid obtained in the above-described (2), 41.1 g of lithium tetrakis(pentafluorophenyl)borate (0.060 mol, produced by Tosoh-Finechem. Corporation), 450 ml of dichloromethane, 450 ml of ion-exchanged water were added, then, by stirring at room temperature for 30 minutes, salt exchanging reaction was carried out. After completion of reaction, organic layer was washed with about 450 ml of ion-exchanged water 4 times. Then, 15 mg of p-methoxyphenol (produced by Wako Pure Chem. Ind., Ltd.) was added, concentrated under reduced pressure, 70.5 g of red solid (yield, 93.0%) in which a chloride ion of dye monomer-I was exchanged to tetrakis(pentafluorophenyl)borate anion was obtained. This is referred to dye monomer M-21.

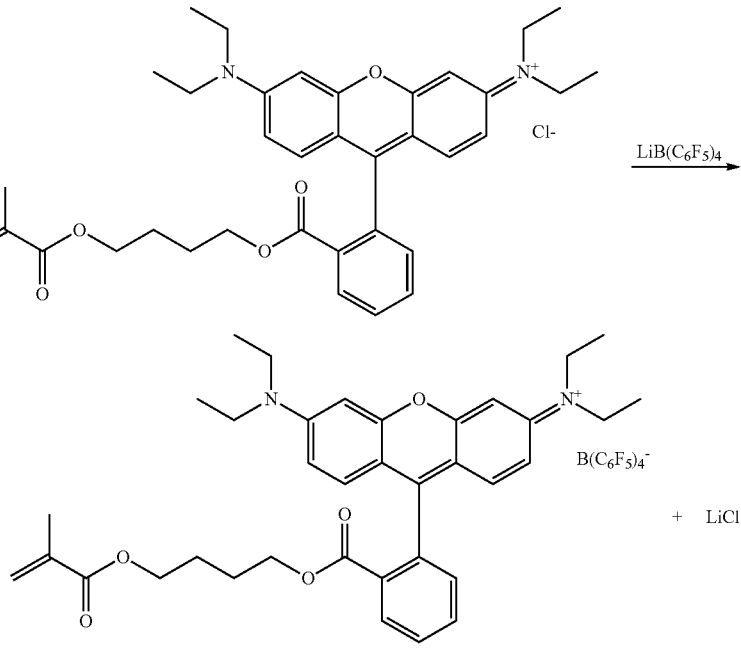

Example 36

Synthesis of Dye Monomer M-22

(1) Synthesis of 6-Hydroxyhexyl Methacrylate

First, 177 g of 1,6-hexanediol (1.5 mol, produced by Wako Pure Chem. Ind., Ltd.), 96 g of I-ethyl-3-(3-dimethylaminopropyl)carbodiimide hydrochloride (0.5 mol, produced by TOYOBO Co., Ltd.), 12 g of N,N-dimethylaminopyridine (produced by Wako Pure Chem. Ind., Ltd.) were dissolved in 2 L of dichloromethane, 43 g of methacrylic acid (0.5 mol, produced by Wako Pure Chem. Ind., Ltd.) was added dropwise, stirred at room temperature for 12 hours. Solvent was distilled off under reducer pressure by using rotary evaporator, purified by silica-gel column chromatography using mixed solution with 1/1 by volume ratio of hexane/ethyl acetate as elution solvent to obtain 56 g of colorless oily 6-hydroxyhexyl methacrylate (yield, 60%).

(2) Addition Reaction to Rhodamine B and Anion Exchange Reaction

According to the method of (2) and (3) in Example 35 except for using 22.4 g of 6-hydroxyhexyl methacrylate (0.12 mol) instead of 19.0 g of 4-hydroxybutyl methacrylate (0.12 mol), monomer was synthesized. The obtained monomer is referred to dye monomer M-22.

Example 37

Synthesis of Dye Monomer M-23

(1) Synthesis of 8-hydroxyoctyl methacrylate

First, 219 g of 1,8-octanediol (1.5 mol, produced by Wako Pure Chem. Ind., Ltd.), 96 g of 1-ethyl-3-(3-dimethylaminopropyl)carbodiimide hydrochloride (0.5 mol, produced by TOYOBO Co., Ltd.), 12 g of N,N-dimethylaminopyridine (produced by Wako Pure Chem. Ind., Ltd.) were dissolved in 2 L of dichloromethane, 43 g of methacrylic acid (0.5 mol, produced by Wako Pure Chem. Ind., Ltd.) was added dropwise, and stirred at room temperature for 12 hours. Solvent was distilled off under reducer pressure by using rotary evaporator, purified by silica-gel column chromatography using mixed solution with 3/2 by volume ratio of hexane/ethyl acetate as elution solvent to obtain 72 g of colorless oily 8-hydroxyoctyl methacrylate (yield, 68%).

(2) Addition Reaction to Rhodamine B and Anion Exchange Reaction according to the method of (2) and (3) in Example 35 except for using 25.7 g of 8-hydroxyoctyl methacrylate (0.12 mol) instead of 19.0 g of 4-hydroxybutyl methacrylate (0.12 mol), monomer was synthesized. The obtained monomer is referred to dye monomer M-23.

Example 38

Synthesis of Dye Monomer M-24

(1) Synthesis of 10-Hydroxydecyl Methacrylate

First, 87 g of 1,10-decanediol (0.5 mol, produced by Wako Pure Chem. Ind., Ltd.), 43 g of methacrylic acid (0.5 mol, produced by Wako Pure Chem. Ind., Ltd.), 5.1 g of p-toluene sulfonic acid (produced by Wako Pure Chem. Ind., Ltd.), 0.6 g of p-methoxyphenol (produced by Wako Pure Chem. Ind., Ltd.) and 150 ml of hexane were mixed, and dehydrated while refluxing for 15 hours. To the obtained reaction solution, 500 ml of 83% methanol aqueous solution was added, stirred sufficiently, then, layer of methanol aqueous solution was washed with hexane 3 times, and 1,12-dodecanediol dimethacrylate of by-product was removed. Next, methanol was distilled off under reduced pressure from the layer of methanol aqueous solution, then, 12-hydroxydodecyl methacrylate was extracted with hexane. Then, solvent was distilled off to obtain 63 g of 10-hydroxydecyl methacrylate (yield, 52%).

(2) Addition Reaction to Rhodamine B and Anion Exchange Reaction

According to the method of (2) and (3) in Example 35 except for using 29.1 g of 10-hydroxydecyl methacrylate (0.12 mol) instead of 19.0 g of 4-hydroxybutyl methacrylate (0.12 mol), monomer was synthesized. The obtained monomer is referred to dye monomer M-24.

Example 39

Synthesis of Dye Monomer M-25

(1) Synthesis of 12-Hydroxydodecyl Methacrylate

First, 101 g of 1, 12-dodecanediol (0.5 mol, produced by Wako Pure Chem. Ind., Ltd.), 43 g of methacrylic acid (0.5 mol, produced by Wako Pure Chem. Ind., Ltd.), 5.1 g of p-toluene sulfonic acid (produced by Wako Pure Chem. Ind., Ltd.), 0.6 g of p-methoxyphenol (produced by Wako Pure Chem. Ind., Ltd.) and 150 ml of hexane were mixed, and dehydrated while refluxing for 15 hours, 500 ml of 83% methanol aqueous solution was added to the obtained reaction solution, stirred sufficiently, then, layer of methanol aqueous solution was washed with hexane 3 times, and 1,12-dodecanediol dimethacrylate of by-product was removed. Next, methanol was distilled off under reduced pressure from the layer of methanol aqueous solution, then, 12-hydroxydodecyl methacrylate was extracted with hexane. Then, solvent was distilled off to obtain 43 g of 12-hydroxydodecyl methacrylate (yield, 32%).

(2) Addition Reaction to Rhodamine B and Anion Exchange Reaction

According to the method of (2) and (3) in Example 35 except for using 32.4 g of 12-hydroxydodecyl methacrylate (0.12 mol) instead of 19.0 g of 4-hydroxybutyl methacrylate (0.12 mol), monomer was synthesized. The obtained monomer is referred to dye monomer M-25.

Example 40

Synthesis of Dye Polymer P-20

To 200 ml round-bottom flask equipped with stirrer, condenser, thermometer, nitrogen introducing pipe, 27.9 g of propylene glycol monomethyl ether acetate (produced by Wako Pure Chem. Ind., Ltd.) was added, heated under nitrogen gas stream until inner temperature reaches 90° C. Then, solution mixed with 48.0 g of dye monomer M-2, 5.0 g of methyl methacrylate (produced by Wako Pure Chem. Ind., Ltd.), 7.0 g of methacrylic acid (produced by Wako Pure Chem. Ind., Ltd.), 9.6 g of dimethyl 2,2'-azobis(2-methylpropionate) (produced by Wako Pure Chem. Ind., Ltd; polymerization inhibitor V-601), and 27.9 g of propylene glycol monomethyl ether acetate (produced by Wako Pure Chem. Ind., Ltd.) were added dropwise into the round-bottom flask over 2 hours. Then, the obtained solution was reacted at 90 (C for 2 hours. After completion of reaction, this was cooled until room temperature, 48.6 g of propylene glycol monomethyl ether acetate was added to dilute, then, dye polymer was obtained. This is referred to dye polymer P-20 (weight ratio: dye monomer M-2/methyl methacrylate/methacrylic aicd=80/8.3.11.7). Further, result of gel permeation chromatography analysis of the obtained polymer solution indicated that weight ratio of unreacted dye monomer contained was 19.6% of total weight.

Example 41 to 45

Synthesis of Dye Polymer P-21 to 25

According to the method in Example 40 except for using 48.0 g of dye monomer M-21 to M-25 instead of 48.0 g of dye monomer M-2, experiments was carried out, respectively to obtain 5 kinds of dye polymers. These are referred to dye polymer P-21, P-22, P-23, P-24, and P-25. Further, result of gel permeation chromatography analysis of the obtained polymer solution of P-21 to P-25 indicated that amounts of unreacted dye monomer contained were 15.2%, 4.9%, 3.2%, 0.9%, and 5.3%, by area %, respectively. Results thereof are shown in Table 5 in conjunction with the result of Example 40.

Example 46

Heat Resistance Evaluation of Dye Polymer P-20 to 25 (230° C. 0.5 hours)

By the same method as Synthetic Example 21 except for using P-21 to P-25 as dye polymer, heat resistance evaluation of dye polymer P-21 to P-25 was carried out. Results thereof are shown in Table 5 in conjunction with the amount of unreacted monomer of Example 40 to 45.

TABLE 5

| Dye Polymer (Dye monomer included) | Example 40 to 45 Amount of unreacted monomer (area %) | Example 46 Dye residual Ratio (%) | Number of atom Between Double Bond in Dye Monomer and Benzene Ring |
|---|---|---|---|
| P-20 (M-2) | 19.8 | 92 | 6 |
| P-21 (M-21) | 15.2 | 94 | 8 |
| P-22 (M-22) | 4.9 | 97 | 10 |
| P-23 (M-23) | 3.2 | 98 | 12 |
| P-24 (M-24) | 0.9 | 97 | 14 |
| P-25 (M-25) | 5.3 | 87 | 16 |

From the above-described result, it was found that the polymer of the present invention reduces amount of residual monomer according to increase of number of atom between double bond in dye monomer (polymerizable group) included and benzene ring (a phenyl group). Among them, when number of atom between double bond and benzene ring is more than 10, amount of residual monomer significantly decreases, when this is 14, amount of residual monomer becomes minimum level, however, it was found that amount of residual monomer adversely increases when this is 16, it was considered that this is an effect due to improving decrease of polymerizability by steric hindrance of dye.

In addition, in the result of heat resistance evaluation, when number of atom between double bond in dye monomer and benzene ring is 6 to 14, excellent heat resistance effect was shown, however, when this is 16, heat resistance is reduced. This cause is not clear, however, it was considered that degradation of dye skeltone itself was promoted because chain length becomes longer, and freedom of polymer movement increases.

The invention claimed is:

1. A polymer having a monomer unit obtained by polymerizing a compound represented by the following general formula (I):

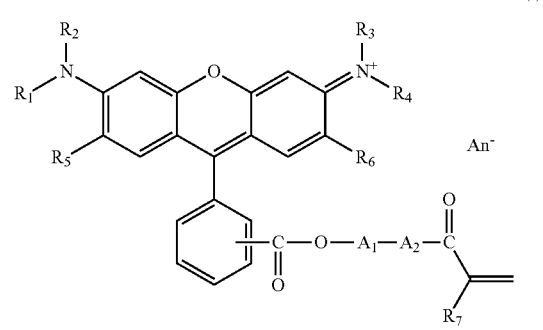

(I)

wherein, $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenoalkyl group having 1 to 6 carbon atoms, a phenyl group or a benzyl group having a substituent or no substituent, and $R_5$ to $R_7$ each independently represent a hydrogen atom or a methyl group, and $A_1$ represents an alkylene group having 1 to 21 carbon atoms which has at least one group of —O—, —OCO—, —COO— and an arylene group in a chain, and, also has a hydroxy group as a substituent, an alkylene group having 1 to 21 carbon atoms which has at least one group of —O—, —OCO—, —COO— and an arylene group in a chain, an alkylene group having 1 to 9 carbon atoms, or an alkylene group having 1 to 6 carbon atoms which has a hydroxy group as a substituent, and $A_2$ represents —NH— or —O—, and An⁻ represents an anion represented by the following general formula (XVI):

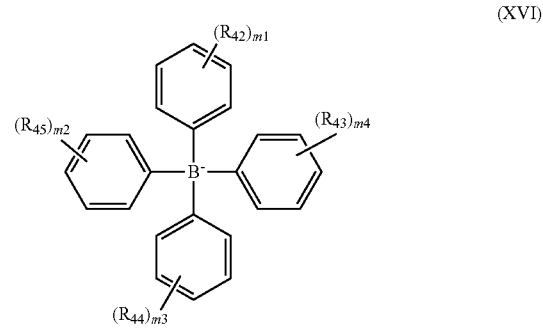

(XVI)

wherein $R_{42}$ to $R_{45}$ each independently represent a halogenated alkyl group of 1 to 3 carbon atoms, a halogen atom or a nitro group, $m_1$ to $m_4$ each independently represent an integer of 1 to 5, and $m_1$ pieces of $R_{42}$, $m_2$ pieces of $R_{43}$, $m_3$ pieces of $R_{44}$ and $m_4$ pieces of $R_{45}$ may be same or different.

2. The polymer according to claim 1, wherein An⁻ is the following anion:

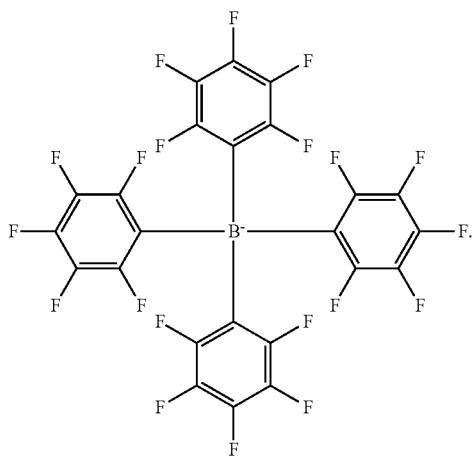 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

3. The polymer according to claim 1, wherein the polymer is a copolymer.

4. The polymer according to claim 3, wherein the copolymer comprises 1 to 2 monomer units obtained by polymerizing the compound represented by the following general formula (II), the general formula (III), the general formula (IV) or the general formula (V) and is changed to the "monomer units obtained by polymerizing the compound represented by the above mentioned general formula (I), as constituent component:

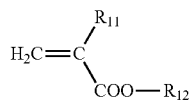

wherein, $R_{11}$ represents a hydrogen atom or a methyl group, $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 10 carbon atoms which has oxygen or no oxygen, a dialkylaminoalkyl group having 3 to 9 carbon atoms, a fluoroalkyl group having 1 to 18 carbon atoms, or an N-alkylenepthalimide group having an alkylene group having 1 to 6 carbon atoms, or the group represented by the following general formula (II-I)

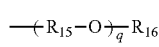

wherein $R_{15}$ represents an alkylene group having 1 to 3 carbon atoms, $R_{16}$ represents a phenyl group which has a hydroxy group as a substituent or no substituent, or an alkyl group having 1 to 3 carbon atoms, and q represents an integer of 1 to 3,
the group represented by the following'general formula (II-II)

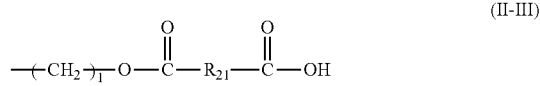

wherein, $R_{17}$ to $R_{19}$ represent an, alkyl group having 1 to 3 carbon atoms, $R_{20}$ represents an alkylene group having 1 to 3 carbon atoms,
or the group represented by the following general formula (II-III)

wherein, 1 represents an integer of 1 to 6, $R_{21}$ represents a phenylene group or a cyclohexylene group;

wherein, $R_{11}$ is the same as the above-described one, $R_{13}$ represents a hydrogen atom or an alkyl group having 1 to 3 carbon atoms, $R_{14}$ represents a hydrogen atom, an alkyl group having 1 to 3 carbon atoms, a dialkylaminoalkyl group having 3 to 7 carbon atoms, or a hydroxyalkyl group having 1 to 6 carbon atoms, and $R_{13}$ and $R_{14}$ may form a motpholino group with a nitrogen atom adjacent to them;

wherein, $R_{31}$ represents a phenyl group, a pyrrolidino group, and $R_{11}$ is the same as the above-described one;

(V)

wherein, $R_{33}$ represents a nitrogen atom or an oxygen atom, j represents 0 when $R_{33}$ is an oxygen atom, and 1 when $R_{33}$ is a nitrogen atom, $R_{32}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 1 to 10 carbon atoms, a halogenated cycloalkyl group having 6 to 7 carbon atoms, an aryl group having 6 to 10 carbon, atoms, an aryl group having 6 to 10 carbon atoms which has an alkyl group having 1 to 6 carbon atoms as a substituent, or a halogenated aryl group having 6 to 10 carbon atoms.

5. A compound represented in the following general formula (I):

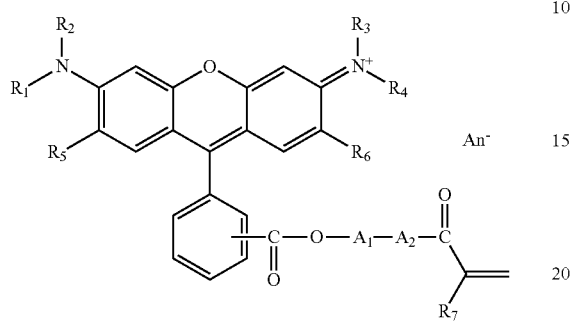

wherein, $R_1$ to $R_4$ each independently represent a hydrogen atom, an alkyl group having 1 to 30 carbon atoms, a hydroxyalkyl group having 1 to 6 carbon atoms, a sulfoalkyl group having 1 to 6 carbon atoms, a carboxyalkyl group having 2 to 7 carbon atoms, a cyanoalkyl group having 2 to 7 carbon atoms, an alkoxyalkyl group having 2 to 6 carbon atoms, a halogenoalkyl group having 1 to 6 carbon atoms, a phenyl group or a benzyl group having a substituent or no substituent, and $R_5$ to $R_7$ each independently represent a hydrogen atom or a methyl group, and $A_1$ represents an alkylene group having 1 to 21 carbon atoms which has at least one group of —O—, —OCO—, —COO— and an arylene group in a chain, and also has a hydroxy group as a substituent, an alkylene group having 1 to 21 carbon atoms which has at least one group of —O—, —OCO—, —COO— and an arylene group in a chain, an alkylene group having 1 to 9 carbon atoms, or an alkylene group having 1 to 6 carbon atoms which has a hydroxy group as a substituent, and $A_2$ represents —NH— or —O—, and An⁻ represents an anion represented by the following general formula (XVI):

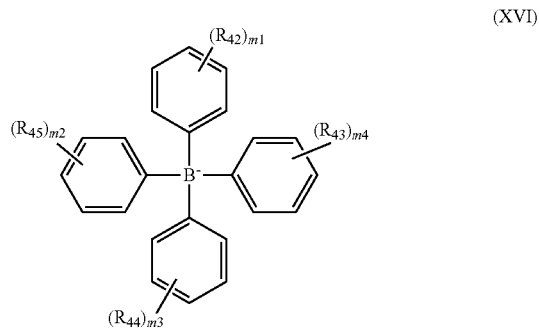

wherein $R_{42}$ to $R_{45}$ each independently represent a halogenated alkyl group of 1 to 3 carbon atoms, a halogen atom or a nitro group, $m_1$ to $m_4$ each independently represent an integer of 1 to 5, and $m_1$ pieces of $R_{42}$, $m_2$ pieces of $R_{43}$, $m_3$ pieces of $R_{44}$ and $m_4$ pieces of $R_{45}$ may be same or different.

6. The compound according to claim 5, wherein $A_2$ is —O—.

7. The compound according to claim 5, wherein $A_1$ is an alkylene group having 1 to 9 carbon atoms.

8. The compound according to claim 5, wherein $R_1$ to $R_4$ are a hydrogen atom or an alkyl group having 1 to 6 carbon atoms.

9. The compound according to claim 5, wherein $R_1$ to $R_4$ are a hydrogen atom or an alkyl group having 1 to 30 carbon atoms, $A_1$ is an alkylene group having 1 to 9 carbon atoms, and $A_2$ is —O—.

10. The compound according to claim 5, wherein An⁻ is the following anion:

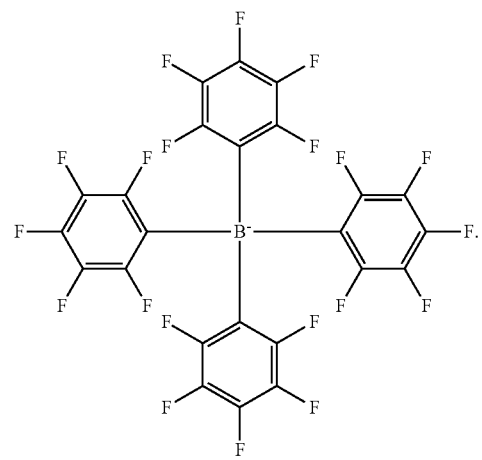 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

11. The compound according to claim 5, wherein the general formula (I) is the following formula:

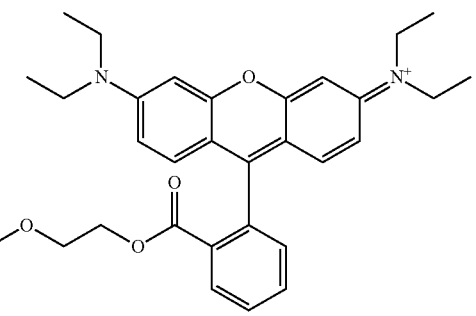

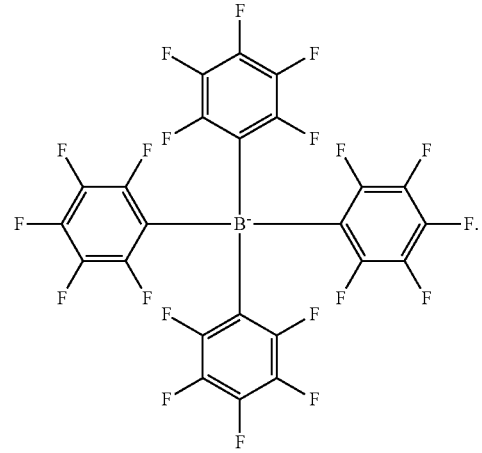

12. A colored composition comprising the polymer according to claim 1.

13. A colored composition for the color filter comprising the polymer according to claim 1.

14. A colored composition comprising the compound according to claim 5.

15. A colored composition for a color filter comprising the compound according to claim 5.

16. The compound according to claim 5, wherein $A_1$ is an alkylene group having 1 to 9 carbon atoms, and $A_2$ is —O—.

17. The compound according to claim 5, wherein $A_1$ is an alkylene group having 1 to 9 carbon atoms, and $A_2$ is —NH—.

* * * * *